United States Patent
Patriciu

(10) Patent No.: US 11,890,129 B2
(45) Date of Patent: Feb. 6, 2024

(54) X-RAY RIPPLE MARKERS FOR X-RAY CALIBRATION

(71) Applicant: KONINKLIJKE PHILIPS N.V., Eindhoven (NL)

(72) Inventor: Alexandru Patriciu, Belmont, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 253 days.

(21) Appl. No.: 17/421,029

(22) PCT Filed: Feb. 14, 2020

(86) PCT No.: PCT/EP2020/053927
§ 371 (c)(1),
(2) Date: Jul. 7, 2021

(87) PCT Pub. No.: WO2020/165422
PCT Pub. Date: Aug. 20, 2020

(65) Prior Publication Data
US 2022/0054103 A1    Feb. 24, 2022

Related U.S. Application Data
(60) Provisional application No. 62/806,005, filed on Feb. 15, 2019.

(51) Int. Cl.
*A61B 6/00* (2006.01)
*G06T 7/37* (2017.01)
(Continued)

(52) U.S. Cl.
CPC ............ *A61B 6/587* (2013.01); *A61B 6/4441* (2013.01); *A61B 6/54* (2013.01); *G01T 7/005* (2013.01);
(Continued)

(58) Field of Classification Search
None
See application file for complete search history.

(56) References Cited

U.S. PATENT DOCUMENTS 10,206,645 B2    2/2019    Claus et al.
10,893,842 B2 *  1/2021    Barak .................... G06T 7/70
(Continued)

FOREIGN PATENT DOCUMENTS

CN    112168357 A    1/2021
WO    2017153839 A1   9/2017
(Continued)

OTHER PUBLICATIONS

International Search Report and Written Opinion of PCT/EP2020/053927, dated May 12, 2020.
(Continued)

*Primary Examiner* — Hoon K Song

(57) ABSTRACT

Various embodiments of the present disclosure include a C-arm registration system employing a controller (70) for registering a C-arm (60) to an X-ray ripple marker (20) including a ripple pattern (50) radially extending from a fixed point (40) of the X-ray ripple marker (20). In operation, the controller (70) identifies the ripple pattern (50) within an X-ray image generated from an X-ray projection by the C-arm (60) and illustrative of a portion or an entirety of the ripple pattern (50), the identification of the ripple pattern (50) within the X-ray image is characteristic of a pose of the X-ray projection by the C-arm (60) relative to the X-ray rippler marker (20). The controller (70) further analyzes the ripple pattern (50) within the X-ray image to derive one or more transformation parameters definitive of the pose of the X-ray projection by the C-arm (60) relative to the (Continued)

X-ray rippler marker (20), and registers the C-arm (60) to the X-ray ripple marker (20) based on the transformation parameter(s).

20 Claims, 31 Drawing Sheets

(51) Int. Cl.
    *G06T 7/70*     (2017.01)
    *G01T 7/00*     (2006.01)

(52) U.S. Cl.
    CPC ............ *G06T 7/37* (2017.01); *G06T 7/70* (2017.01); *G06T 2207/10116* (2013.01); *G06T 2207/20056* (2013.01); *G06T 2207/30204* (2013.01); *G06T 2207/30244* (2013.01)

(56) References Cited

U.S. PATENT DOCUMENTS

| | | | |
|---|---|---|---|
| 2004/0082854 A1 | 4/2004 | Essenreiter | |
| 2006/0115054 A1* | 6/2006 | Yatsenko | A61B 6/4291 378/207 |
| 2008/0285724 A1 | 11/2008 | Dehler | |
| 2010/0284601 A1 | 11/2010 | Rubner | |
| 2012/0281808 A1* | 11/2012 | Graumann | A61B 6/584 378/41 |
| 2016/0045269 A1 | 2/2016 | Elhawary | |
| 2017/0035382 A1 | 2/2017 | Zhang | |
| 2021/0322104 A1* | 10/2021 | Herrmann | G06T 7/596 |
| 2022/0273375 A1* | 9/2022 | Mucha | A61B 34/20 |

FOREIGN PATENT DOCUMENTS

| | | |
|---|---|---|
| WO | 2018078445 A2 | 5/2018 |
| WO | 2019023375 A2 | 1/2019 |
| WO | 2020159984 A1 | 8/2020 |
| WO | 2020165422 A1 | 8/2020 |
| WO | 2020185048 A2 | 9/2020 |

OTHER PUBLICATIONS

Steger, Tenna et al "Marker Detection Evaluation by Phantom and Cadaver Experiments for C-arm Pose Estimation Pattern", SPIE—International Society for Optical Engineering, vol. 8671, Mar. 2012.
Calvet, Lilian et al "Detection and Accurate Localization of Circular Fiducials under Highly Challenging Conditions", 2016 IEEE Conference on Computer Vision and Pattern Recognition, pp. 562-570 Jun. 27, 2016.
Kainz, Bernhard et al "Fast Marker Based C-Arm Pose Estimation", International Conference on Financial Cryptography and Data Security, Sep. 6, 2008, pp. 652-659.

* cited by examiner

FLOWCHART 80

S82: IDENTIFY RIPPLE MARKER/PATTERN IN X-RAY IMAGE

S84: DERIVE TRANSFORMATION PARAMETER(S) FROM RIPPLE PATTERN

S86: REGISTER X-RAY RIPPLE MARKER AND X-RAY C-ARM

S88: REMOVE X-RAY RIPPLE MARKER FROM X-RAY IMAGE

TERMINATE

X-RAY RIPPLE MARKERS FOR X-RAY CALIBRATION

CROSS-REFERENCE TO PRIOR APPLICATIONS

This application is the U.S. National Phase application under 35 U.S.C. § 371 of International Application No. PCT/EP2020/053927, filed on Feb. 14, 2020, which claims the benefit of U.S. Provisional Patent Application Ser. No. 62/806,005, filed Feb. 15, 2019. These applications are hereby incorporated by reference herein.

FIELD OF THE INVENTION

The present disclosure generally relates to X-ray calibration. The present disclosure specifically relates to an imaging of an X-ray ripple marker for X-ray calibration.

BACKGROUND OF THE INVENTION

X-ray C-arm systems are frequently used in minimally invasive surgical procedures (e.g., orthopedic procedures, vascular interventions, etc.) for enabling surgeons to see inside a patient body by taking X-ray images from arbitrary directions. More particularly, a mobile C-arm usually has wheels to provide mobility around the room and once positioned, the mobile C-arm allows the user to adjust the position of the C-arm in five (5) directions. While this provides flexibility in the execution of minimally invasive surgical procedures, the exact position and angle of the X-ray projection is not known. This precludes the user from employing advanced tools including making true three-dimensional ("3D") measurements, large field of view imaging, dynamic overlay of pre-operative or intraoperative information, and target localization for image guided intervention. Thus, after a positioning of the mobile C-arm with respect to the patient body, there has been a need to compute a pose of the X-ray projection with respect to a fixed coordinate system, which is conventionally called C-arm Registration. Specifically, a mobile C-arm position is computed with respect to a fixed coordinate system and described by a homogeneous transformation composed of a translation vector ($t \in R^3$) and a rotation matrix ($R \in SO(3)$). Therefore, the task has been to compute the pair (t, R) that accurately describes the position of the mobile C-arm with respect to the fixed coordinate system.

One historic approach for solving the C-arm Registration required an installation of hardware on the C-arm (e.g., optical tracking markers, inertial markers, etc.). This approach requires the addition of multiple components to the room and often negatively impacts the workflow for the procedure.

A current practice for C-Arm Registration is to provide a marker having a fixed position in the operating space (e.g., a marker attached to a robot or an operating table), and to generate an X-ray image of features of the marker to perform the C-arm Registration (e.g., steel balls or features of a known geometry). For such markers, there are cost-benefit tradeoffs with respect to a required registration accuracy, the number of opaque features on the marker, size of the marker, impact to the workflow, and impact to the x-ray image.

SUMMARY OF THE INVENTION

While known C-arm Registration methods have proven to be beneficial, there remains a need for improved techniques for providing accurate and reliable C-arm Registration, particularly for mobile C-arms. The present disclosure teaches a X-ray ripple marker that creates one or more X-ray imaged wave(s) with characteristics that are a function of a pose of an X-ray projection by the C-arm with respect to the X-ray ripple marker. In some implementations, X-ray ripple marker employs additional features (e.g., copper or steel balls) that improve registration algorithm robustness.

One embodiment of the present disclosure is an C-arm registration system employing a C-arm registration controller for registering a C-arm to an X-ray ripple marker including a ripple pattern radially extending from a fixed point of the X-ray ripple marker. The C-arm registration controller is configured to identify the ripple pattern within an X-ray image generated from an X-ray projection by the C-arm and illustrative of a portion or an entirety of the marker, to analyze the ripple pattern within the X-ray image to derive one or more transformation parameters, and to register the C-arm to the X-ray ripple marker based on the transformation parameter(s).

The identification of the ripple pattern within the X-ray image is characteristic of a pose of the X-ray projection by the C-arm relative to the X-ray rippler marker, and the transformation parameter(s) is(are) definitive the pose of the X-ray projection by the C-arm relative to the X-ray rippler marker.

The pose of the X-ray projection by the C-arm relative to the X-ray ripple marker encompasses a location and/or an orientation of the X-ray projection by the C-arm within a coordinate system associated with the X-ray ripple marker (e.g., a coordinate system having the fixed point of the X-ray ripple marker as the origin or a coordinate system of an intervention device such as an intervention robot system having the X-ray ripple marker attached thereto).

In one embodiment of the C-arm registration system, the C-arm registration controller employs non-transitory machine-readable storage medium encoded with instructions for execution by one or more processors to identify the ripple pattern within an X-ray image generated from an X-ray projection by the C-arm and illustrative of a portion or an entirety of the X-ray ripple marker, to analyze the ripple pattern within the X-ray image to derive the transformation parameter(s), and to register the C-arm to the X-ray ripple marker based on the transformation parameter(s).

Another embodiment of the present disclosure is an C-arm registration method executable by the C-arm registration controller. In operation, C-arm registration controller identifies the ripple(s) pattern within an X-ray image generated from an X-ray projection by the C-arm and illustrative of a portion or an entirety of the marker, analyzes the ripple pattern within the X-ray image to derive the transformation parameter(s), and registers the C-arm to the X-ray ripple marker based on the transformation parameter(s).

For various embodiments of the present disclosure, the ripple pattern includes a plurality of concentric circular ripples, a first series of concentric arc ripples, and/or a second series of concentric arc ripples dissimilar to the first series of concentric arc ripples in frequency, phase and/or amplitude.

For various embodiments of the present disclosure, the X-ray ripple marker further includes a chirp pattern and/or a landmark pattern axially aligned with the ripple pattern.

For purposes of the description and claims of the present disclosure:

(1) terms of the art including, but not limited to, "marker", "X-ray", "C-arm", "registration", "calibration", "robot" and "transformation parameter", are to be interpreted as known in the art of the present disclosure and as exemplary described in the present disclosure;

(2) the term "X-ray ripple marker" broadly encompasses a marker incorporating a ripple pattern radially extending from a fixed point of the marker for creating X-ray imaged wave(s) with characteristics that are a function of a position of an X-ray projection by a C-arm with respect to the X-ray ripple marker in accordance with various aspects of the present disclosure as exemplary described herein;

(3) the term "wave" includes broadly encompasses a frequency signal of any type including, but not limited to, a fixed frequency signal and a swept frequency signals (e.g., chirps).

(4) the term "ripple pattern" broadly encompasses an arrangement one or more circular ripples and/or one or more arc ripples radially extending from a fixed point of the X-ray ripple marker whereby a frequency, a phase and/or an amplitude of the circular/arc ripple(s) serve to create the X-ray imaged wave(s) in accordance with various aspects of the present disclosure as exemplary described herein;

(5) the term "chirp pattern" broadly encompasses an arrangement of one or more chirps to generate a chirp signal representative of an additional dimension of freedom of the transformation of the X-ray projection by the C-arm with respect to the X-ray ripple marker;

(6) the term "landmark pattern" broadly encompasses an arrangement of one or more landmarks disposed on the X-ray ripple marker to find one or more points on the X-ray ripple marker (e.g., a center point of the X-ray ripple marker).

(7) the term "controller" broadly encompasses all structural configurations, as understood in the art of the present disclosure and as exemplary described in the present disclosure, of main circuit board or integrated circuit for controlling an application of various aspects of the present disclosure as exemplary described in the present disclosure. The structural configuration of the controller may include, but is not limited to, processor(s), computer-usable/computer readable storage medium(s), an operating system, application module(s), peripheral device controller(s), slot(s) and port(s). A controller may be housed within or linked to a workstation. Examples of a "workstation" include, but are not limited to, an assembly of one or more computing devices, a display/monitor, and one or more input devices (e.g., a keyboard, joysticks and mouse) in the form of a standalone computing system, a client computer of a server system, a desktop or a tablet;

(8) the term "application module" broadly encompasses an application incorporated within or accessible by a controller consisting of an electronic circuit (e.g., electronic components and/or hardware) and/or an executable program (e.g., executable software stored on non-transitory computer readable medium(s) and/or firmware) for executing a specific application; and (9) the terms "data" and "signal" broadly encompasses all forms of a detectable physical quantity or impulse (e.g., voltage, current, or magnetic field strength) as understood in the art of the present disclosure and as exemplary described in the present disclosure for transmitting information and/or instructions in support of applying various aspects of the present disclosure as subsequently described in the present disclosure. Data/signal communication components of the present disclosure may involve any communication method as known in the art of the present disclosure including, but not limited to, data/signal transmission/reception over any type of wired or wireless datalink/signal link and a reading of data/signal uploaded to a computer-usable/computer readable storage medium.

The foregoing embodiments and other embodiments of the inventions of the present disclosure as well as various structures and advantages of the inventions of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the inventions of the present disclosure being defined by the appended claims and equivalents thereof.

BRIEF DESCRIPTION OF THE DRAWINGS

FIGS. 11A-11D illustrate an exemplary marker position approximation/refinement of FIG. 9 in accordance with various aspects of the present disclosure.

DETAILED DESCRIPTION OF THE PREFERRED EMBODIMENTS

To facilitate an understanding of various aspects of the present disclosure, the following description of FIGS. 1-4C teaches embodiments of an X-ray ripple marker of the present disclosure. From this description, those having ordinary skill in the art will appreciate how to apply the various aspects of the present disclosure for making and using additional embodiments of X-ray ripple markers of the present disclosure.

Figure 1:
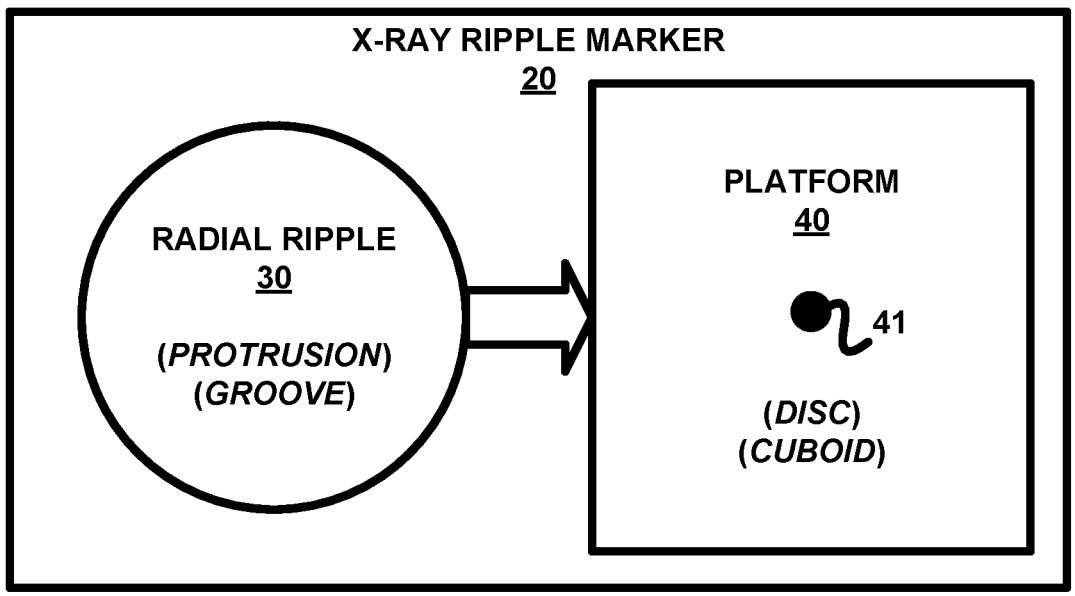
FIG. 1 illustrates an exemplary embodiment of an X-ray ripple marker in accordance with various aspects of the present disclosure.

Referring to FIG. 1, an X-ray ripple marker 20 of the present disclosure employs one or more radial ripples 30 integrated within a platform 40 and radially extending from a fixed point 41 of platform 40 (e.g., a center point of platform 40).

In practice, platform 40 may have any size and shape that facilitates an X-ray imaging of radial ripple(s) 30 radially extending from fixed point 41 of platform 40. For example, platform 40 may have a disc shape or a cuboid shape with radial ripple(s) 30 integrated onto a same side surface of the disc or the cuboid, and radially extending from any fixed point on that side surface of the disc or the cuboid (e.g., a center of the disc or the cuboid). The size of the disc and cuboid is not limited by the X-ray imaging space of one or particular types of X-ray imaging systems or generic to all X-ray imaging systems.

Figure 2A:
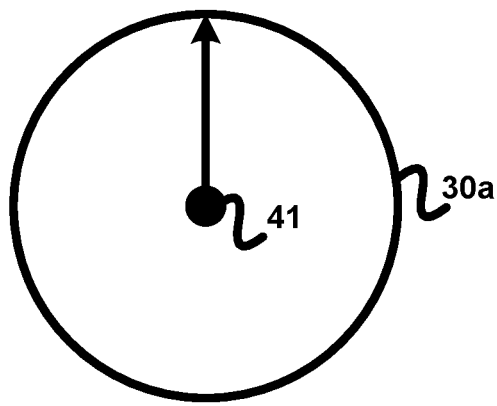
FIGS. 2A-2D illustrate exemplary embodiments of radial ripples in accordance with various aspects of the present disclosure.
Figure 2B:
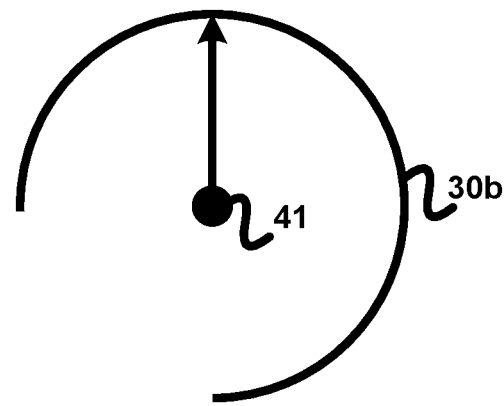
Figure 2C:
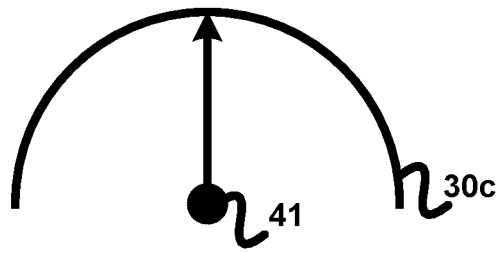
Figure 2D:
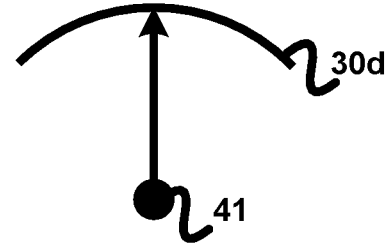

Also in practice, a radial ripple 30 may have any shape and dimensions that partially or fully encircles the fixed point. For example, FIG. 2A shows a radial ripple 30a as a circle fully encircling a fixed point 41 of platform 40, FIG. 2B shows a radial ripple 30b as a 270° arc partially encircling the fixed point 41 of platform 40, FIG. 2C shows a radial ripple 30c as a 180° arc partially encircling the fixed point 41 of platform 40 and FIG. 2D shows a radial ripple 30d as a 90° arc partially encircling the fixed point 41 of platform 40.

Figure 3A:
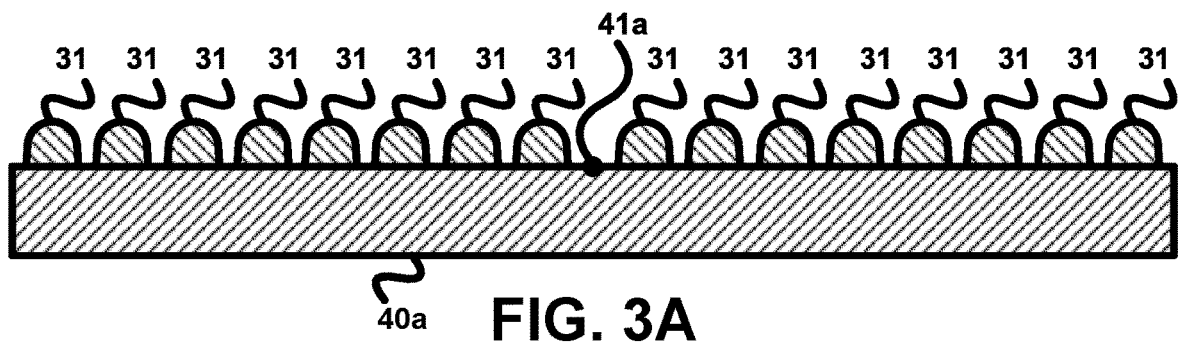
FIGS. 3A and 3B illustrate exemplary embodiments of platforms in accordance with various aspects of the present disclosure.
Figure 3B:
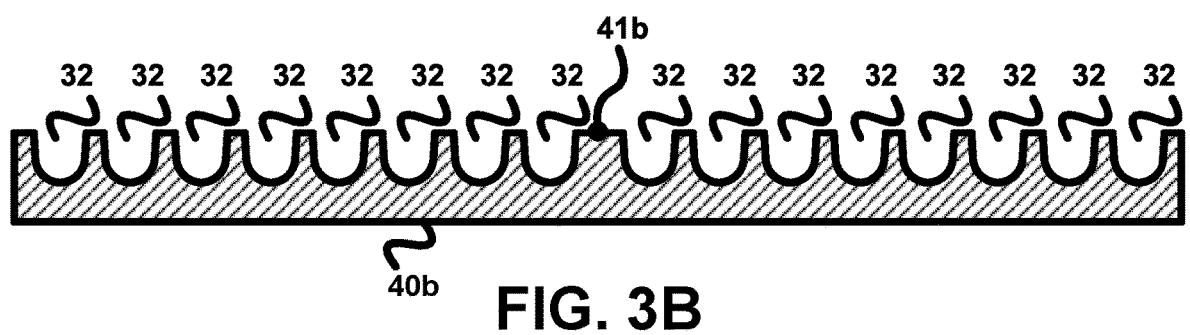

Further in practice, a radial ripple 30 may be integrated into platform 40 in any manner than facilitates an X-ray imaging of X-ray ripple marker 20 that distinguishes the radial ripple(s) 30 from the platform 40 within the X-ray image. For example, FIG. 3A shows a cross-section of a platform 40a having a plurality of radial ripples 30 as protrusions 31 upwardly extending from a top surface of platform 40a relative to a fixed point 41a, and FIG. 3B shows a cross-section of a platform 40b having a plurality of radial ripples as grooves 32 downwardly extending into a top surface of platform 40b relative to a fixed point 41b. Also by example, an X-ray ripple marker 20 may employ one or more radial ripples 30 as protrusions and one or more additional radial ripples 30 as grooves.

Referring back to FIG. 1, for C-arm registration purposes, radial ripple(s) 30 are integrated onto platform 40 to form a ripple pattern that create(s) X-ray imaged wave(s) with characteristics that are a function of a position of an X-ray projection of a C-arm with respect to the X-ray ripple marker 20 as will be further described in the present disclosure with the C-arm registration description of FIGS. 5-18.

Figure 4A:
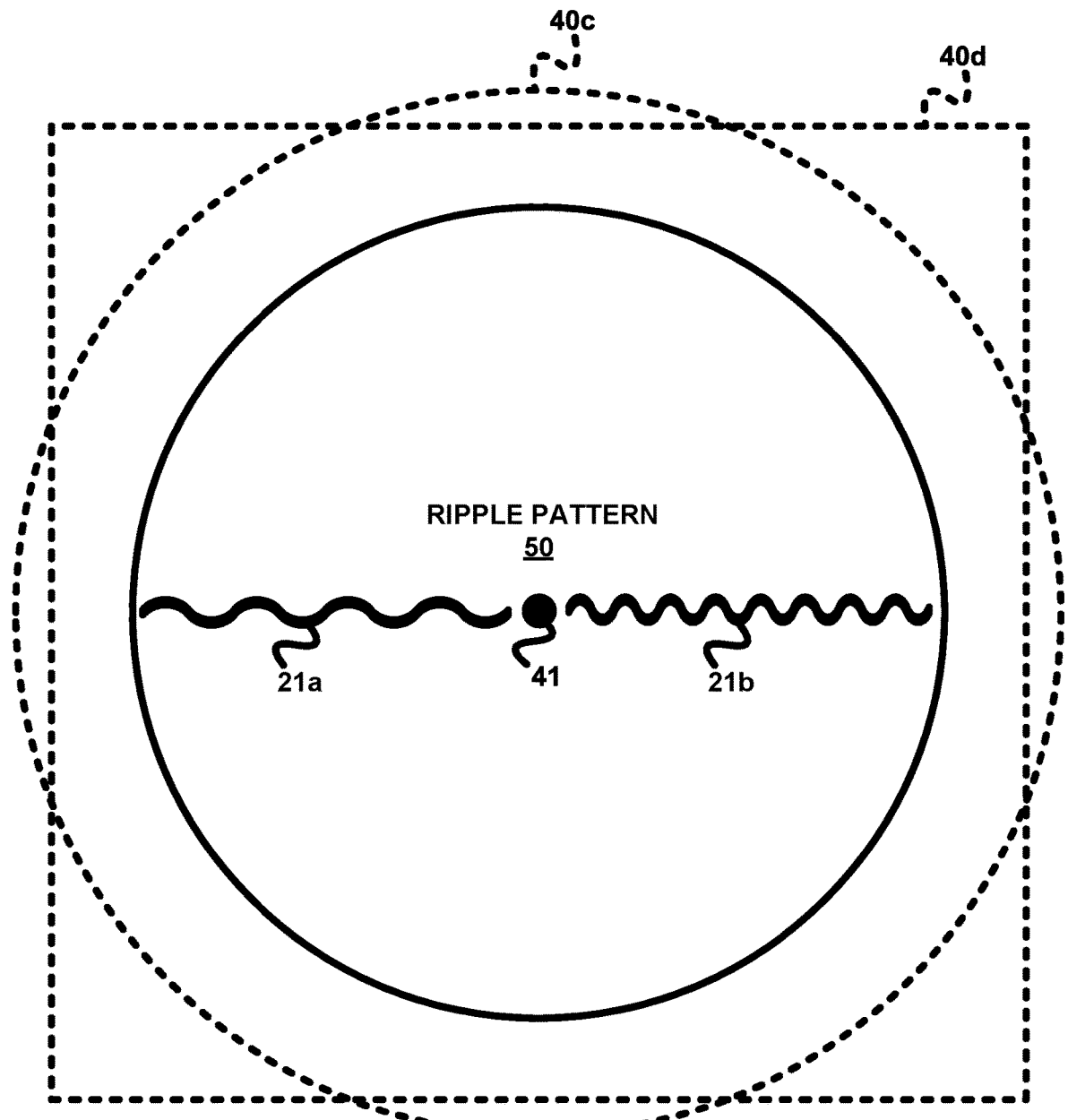
FIGS. 4A-4G illustrates exemplary embodiments of the X-ray ripple marker of FIG. 1 in accordance with various aspects of the present disclosure.

For example, FIG. 4A illustrates a radial pattern 50 of radial ripple(s) 30 being integrable onto a surface of a disc 40c or a platform 40b for creating X-ray imaged wave(s) as symbolically shown by waves 21a and 21b.

In practice, a frequency, a phase and/or an amplitude of an X-ray imaged wave may be the characteristic(s) that is(are) a function of a position of an X-ray projection of a C-arm with respect to the X-ray ripple marker 20.

Further in practice, relative frequencies, relative phases and/or relative amplitudes of two or more X-ray imaged wave(s) may be the characteristics that is(are) a function of a position of an X-ray projection of a C-arm with respect to the X-ray ripple marker 20.

Figure 4B:
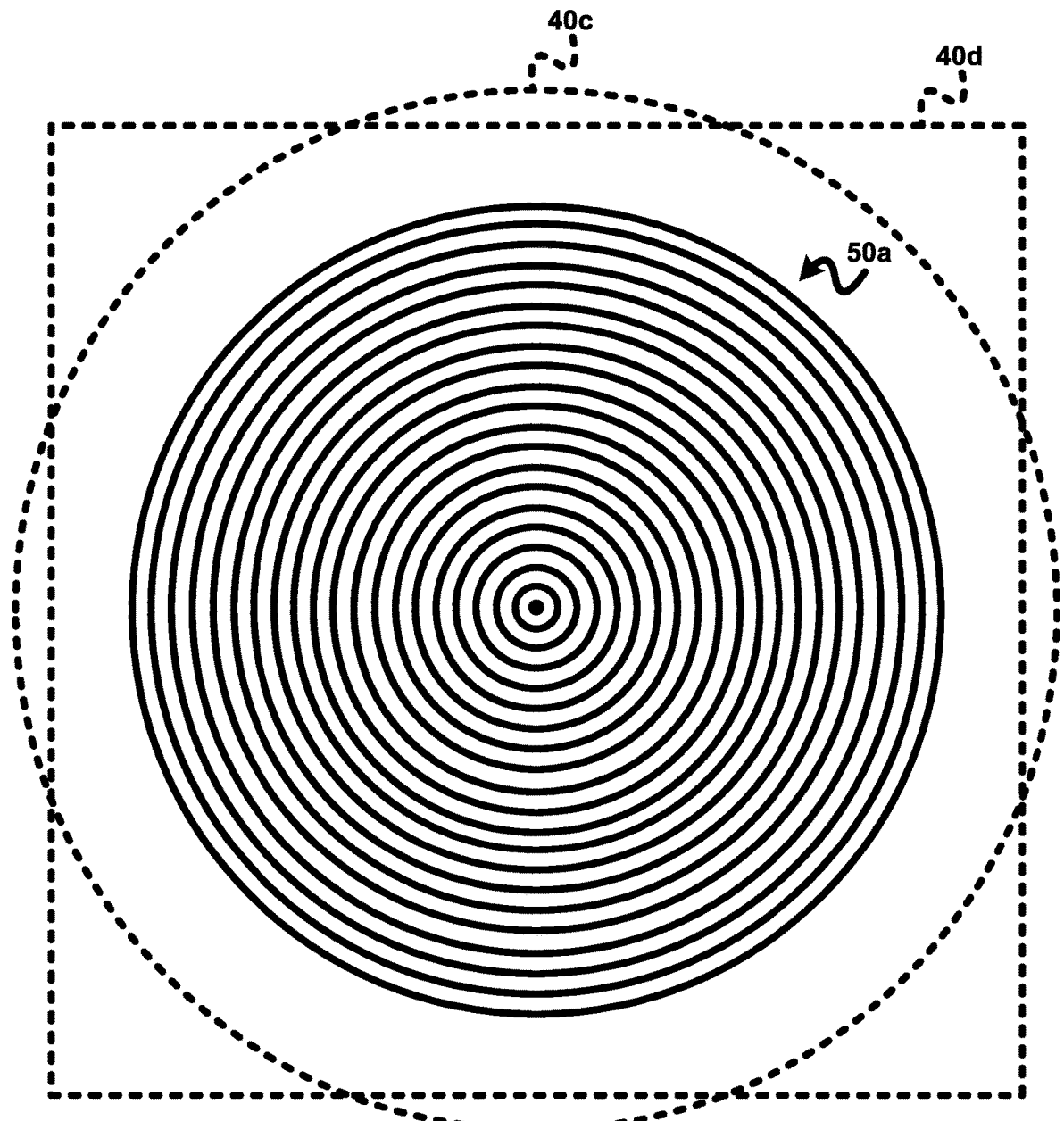

In one embodiment of ripple pattern 50 as shown in FIG. 4B, a ripple pattern 50a of twenty (20) concentric circular radial ripples as integrated on disc 40c or cuboid 40d, which provides a five (5) degree of freedom transformation of an X-ray projection of a C-arm to the coordinate system associated with the marker using a single X-ray image.

Figure 4C:
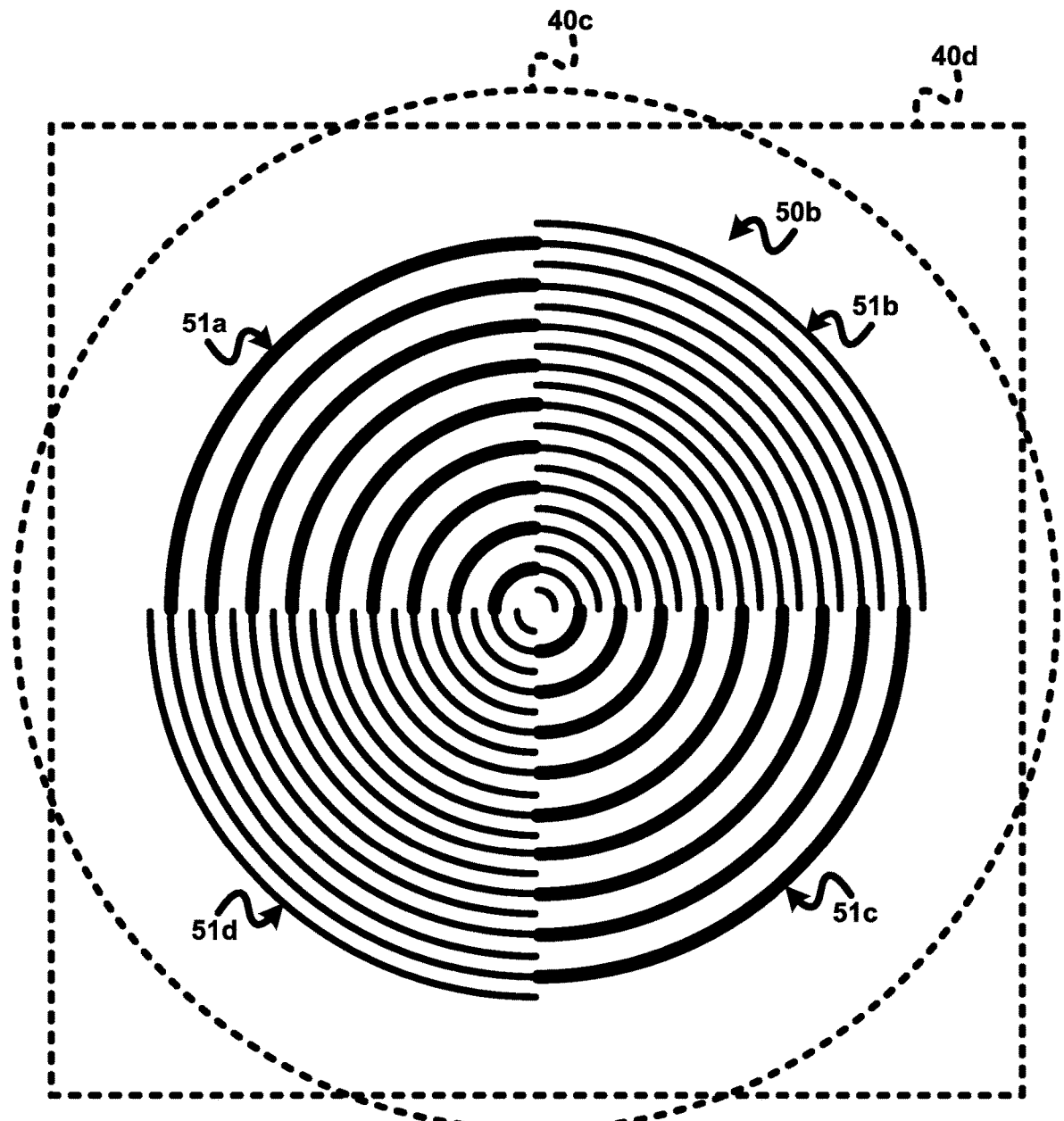

In a second embodiment of ripple pattern 50 as shown in FIG. 4C, a ripple pattern 50b includes a series 51a of nine (9) concentric 90° arc radial ripples, a series 51b of seventeen (17) concentric 90° arc radial ripples, a series 51c of nine (9) concentric 90° arc radial ripples and a series 51d of seventeen (17) concentric 90° arc radial ripples. Ripple pattern 50b also provides a five (5) degree of freedom transformation of an X-ray projection of a C-arm to the coordinate system associated with the marker using a single X-ray image.

Still referring to FIG. 4C, in practice of a ripple pattern 50 having a plurality of arc series, an arc series may be identical to one or more other arc series in terms of frequency, phase and amplitude, or the arc series may be dissimilar to or more other arc series in terms of frequency, phase and/or amplitude.

Arc series 51a and arc series 51c are identical to each other in terms of frequency, phase and amplitude. Arc series 51a and arc series 51c are identical to arc series 51b and 51d in terms of phase, but dissimilar to arc series 51b and arc series in terms of 51d in frequency and amplitude.

Figure 4D:
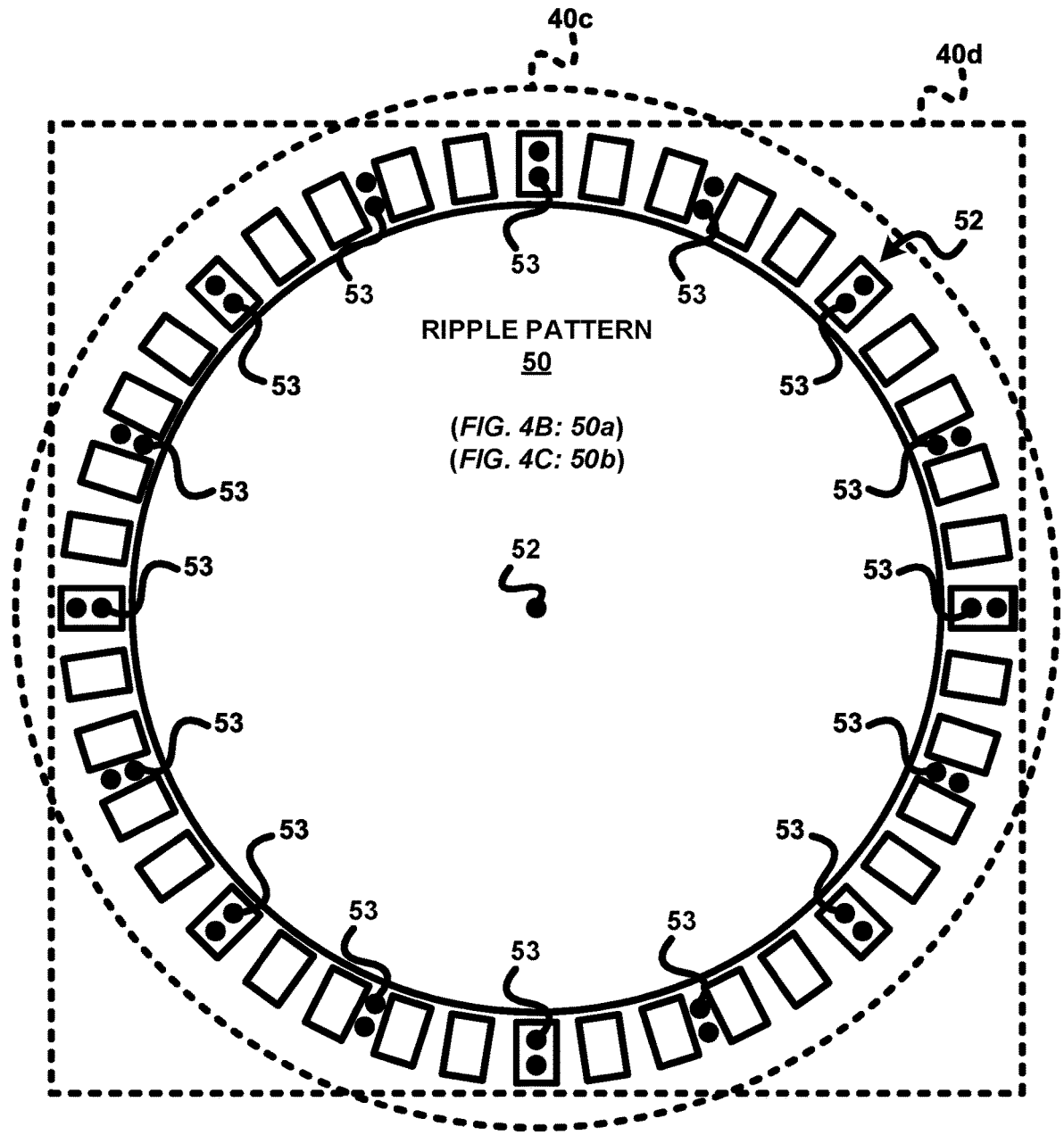

For any embodiment of ripple pattern 50 (e.g., ripple pattern 50a of FIG. 4A and ripple pattern 50b of FIG. 4B), a chirp pattern of chirps (e.g., protrusions and/or grooves) may be axially aligned with a ripple pattern 50 to provide a sixth degree of freedom transformation of an X-ray projection of a C-arm to the coordinate system associated with the marker using a single X-ray image. For example, FIG. 4D shows a circular chirp pattern 52 of forty (40) chirps encircling a perimeter of ripple pattern 50.

In practice, a chirp may be disposed on the same side surface of the platform as ripple pattern 50, and/or a chirp may be disposed on a side surface of the platform opposing the ripple pattern 50.

For any embodiment of ripple pattern 50 (e.g., ripple pattern 50a of FIG. 4A and ripple pattern 50b of FIG. 4B), a landmark pattern (e.g., a pattern of copper balls) may be axially aligned with the ripple pattern 50 to facilitate a finding of the fixed point of the platform and/or for C-arm registration computations including, but not limited to, a final optimization and registration error estimation. For example, FIG. 4D shows a landmark pattern of a series of sixteen (16) pairings of copper balls 53 encircling a perimeter of ripple pattern 50.

In practice, the landmark pattern may be disposed on the same side surface of the platform as ripple pattern 50, and/or the landmark pattern may be disposed on a side surface of the platform opposing the ripple pattern 50.

From the description of FIGS. 4A-4C, those having ordinary skill in the art will appreciate the broad scope of embodiments of X-ray ripple markers of the present disclosure.

Figure 4E:
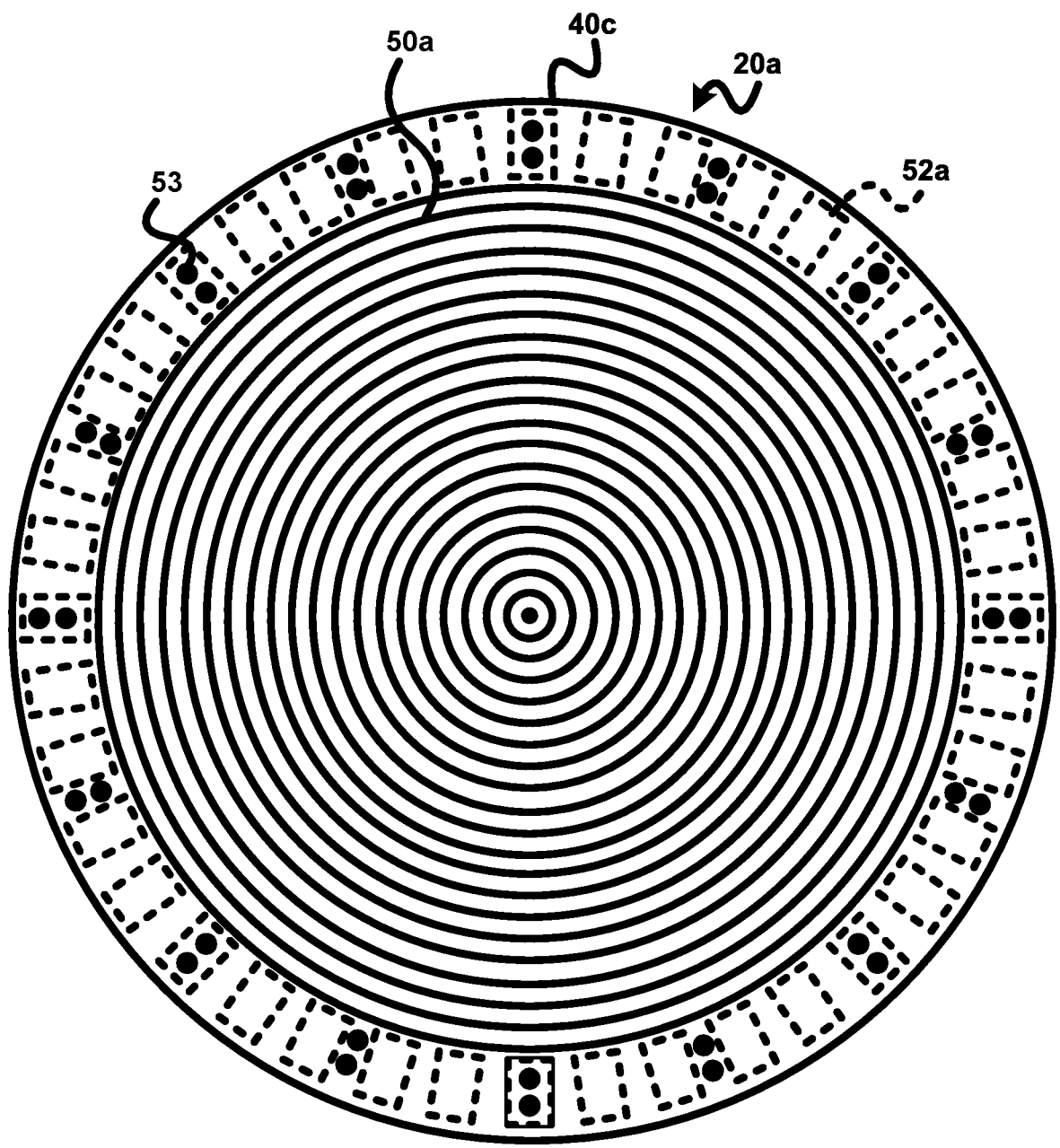

For example, FIG. 4E shows an exemplary X-ray ripple marker 20a incorporating a protrusion embodiment 31 of ripple pattern 50a (FIG. 4B) integrated on disc 40c, a protrusion embodiment 52a of circular chirp pattern 52 (FIG. 4D) disposed on a same side surface or an opposite side surface of disc 40c as ripple pattern 50a, and the landmark pattern of copper balls 53 of FIG. 4D encircling a perimeter of ripple pattern 50.

Figure 4F:
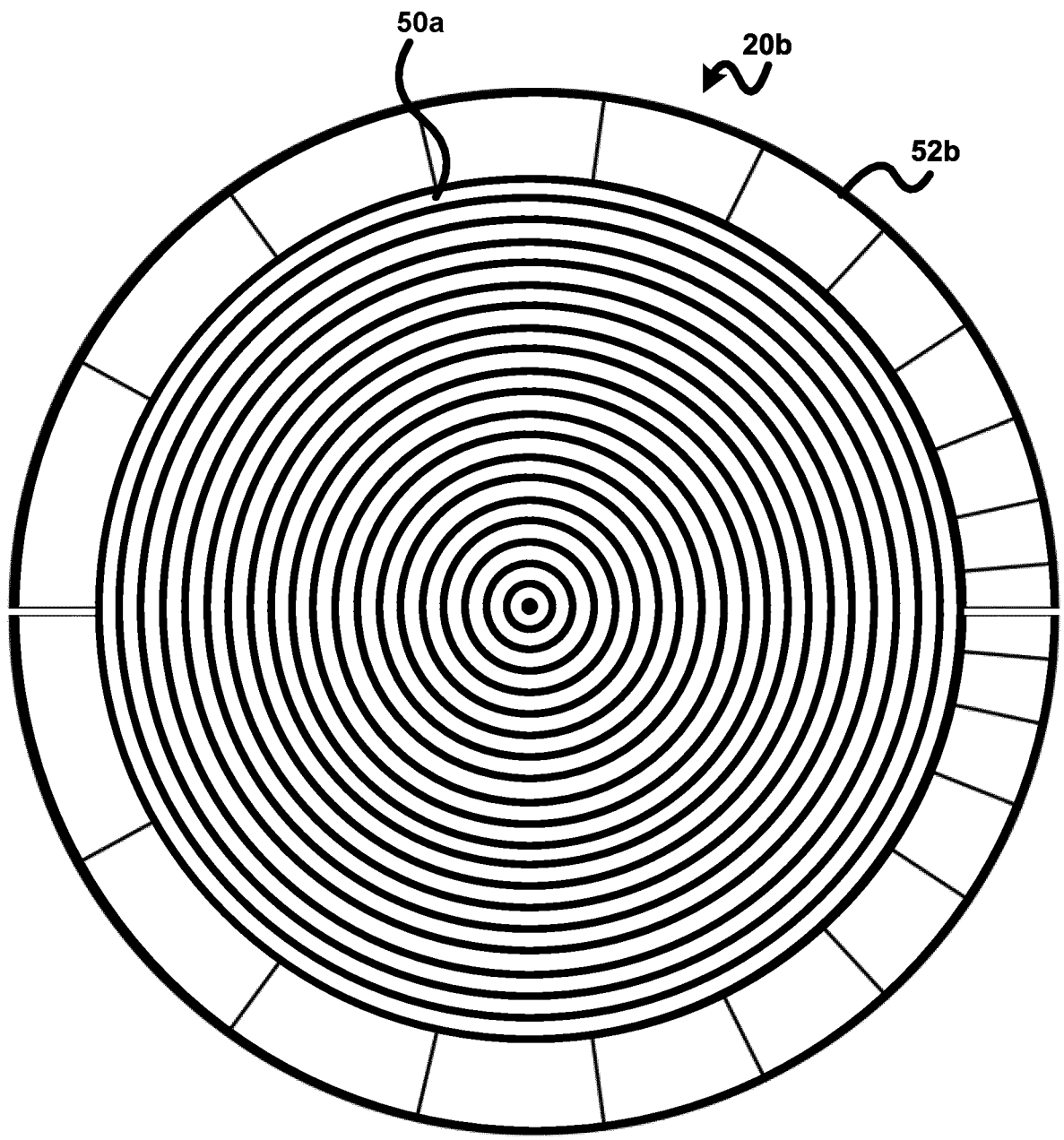

By additional example, FIG. 4F shows an exemplary X-ray ripple marker 20b incorporating a protrusion embodiment 31 of ripple pattern 50a (FIG. 4B) integrated on disc 40c, and a progressive spacing protrusion embodiment 52b of circular chirp pattern 52 (FIG. 4D) disposed on the same side surface or the opposite side surface of disc 40c as ripple pattern 50a.

Figure 4G:
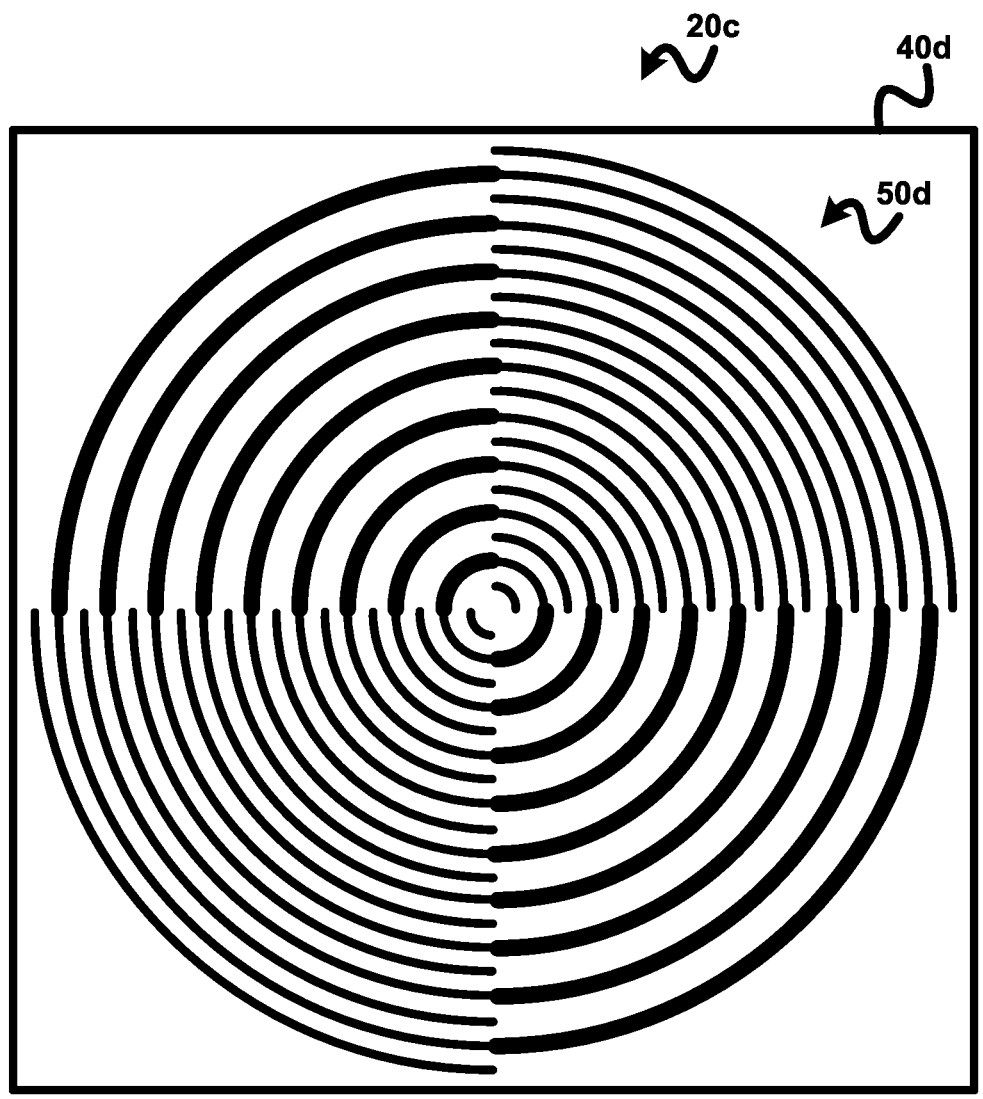

By further example, FIG. 4G shows an exemplary X-ray ripple marker 20c incorporating a protrusion embodiment 50d of ripple pattern 50b (FIG. 4C) integrated on cuboid 40d.

To further facilitate an understanding of various aspects of the present disclosure, the following description of FIGS. 5-18B teaches embodiments of a C-arm registration of the present disclosure. From this description, those having ordinary skill in the art will appreciate how to apply various aspects of the present disclosure for making and using additional embodiments of C-arm registration of the present disclosure.

While X-ray ripple marker 20a of FIG. 4D and X-ray ripple marker 20b of FIG. 4E will be utilized for purposes of describing embodiments of a C-arm registration of the present disclosure, those having ordinary skill in the art will appreciate how to apply various aspects of the present disclosure for executing a C-arm registration of the present disclosure using any embodiment of an X-ray ripple marker of the present disclosure.

Referring to FIG. 5, a C-arm registration of the present disclosure is implemented in a patient-less mode and a patient mode.

Generally in the patient-less mode, an X-ray ripple marker 20 (e.g., X-ray ripple marker 20a of FIG. 4E or X-ray ripple marker 20b of FIG. 4F as shown) has a fixed position within an intervention space (e.g., an attachment to an operating table, a rail, a drape, or an intervention robot). An X-ray source 61 and an X-ray detector 62 of a C-arm 60 are translated and/or rotated to a position to generate an X-ray image 63 of a ripple pattern 50 of X-ray ripple marker 20. A C-arm registration controller 70 acquires X-ray image 63 and executes a C-arm to marker registration 71 of the present disclosure delineating a position of an X-ray projection by C-arm 60 with respect to the X-ray ripple marker 20 as will be further described in the present disclosure. Subsequently, X-ray ripple marker 20 is removed from an imaging space of C-arm 60 whereby a patient may be positioned within the imaging space of C-arm 60 to thereby perform an intervention based on the C-arm registration involving a generation of X-ray image(s) 64.

Generally in the patient mode, an X-ray ripple marker 20 (e.g., X-ray ripple marker 20a of FIG. 4E or X-ray ripple marker 20b of FIG. 4F as shown) has a fixed position within an intervention space (e.g., an attachment to an operating table or an intervention robot) and a body part of interest of a patient is positioned above and adjacent X-ray ripple marker 20 (body part not shown for clarity of the marker). The X-ray source 61 and the X-ray detector 62 of C-arm 60 are translated and/or rotated to a position to generate an X-ray image 63 of a ripple pattern 50 of X-ray ripple marker 20. A C-arm registration controller 70 acquires X-ray image 65a and executes a C-arm to marker registration 71 of the present disclosure delineating a position of an X-ray projection by C-arm 60 with respect to the X-ray ripple marker 20 as will be further described in the present disclosure. C-arm registration controller 70 may additionally executes a ripple marker removal 72 of the present disclosure removing X-ray ripple marker 20 (or at least the ripple pattern 50) from X-ray image 65a to render an X-ray image 65b for display during an intervention based on the C-arm registration of the present disclosure.

Figures 6, 7:
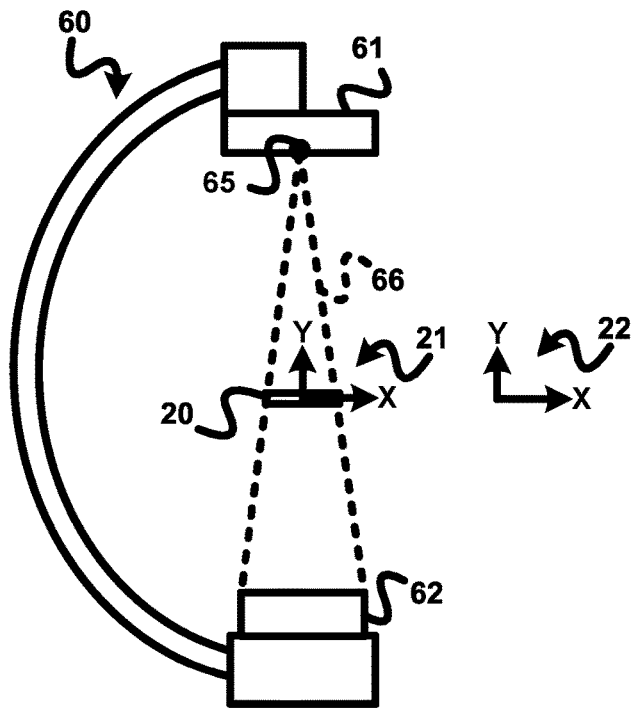
FIG. 6 illustrates a first exemplary embodiment of an X-ray projection by a C-arm in accordance with the various aspects of the present disclosure.
FIG. 7 illustrates a flowchart representative of a first exemplary embodiment of an C-arm registration of FIG. 5 in accordance with various aspects of the present disclosure.

More particularly to both the patient-less mode and the patient mode, as shown in FIG. 6, the C-arm to marker registration 71 involves registering a position of an X-ray projection relative to an X-ray ripple marker 20 of the present disclosure within a 3D coordinate system 21 or 3D coordinate system 22 (only the Y-axis and the X-axis are shown, the Z-axis is not shown).

In practice, the X-ray projection may originate at any point of the X-ray source 61, such as, for example, a focal spot 65 as shown in FIG. 6.

In practice, X-ray ripple marker 20 may establish coordinate system 21 having a fixed point of the X-ray ripple marker 20 as the origin of coordinate system 21, or alternatively, X-ray ripple marker 20 may be calibrated with a coordinate system 22 of an intervention device (e.g., an intervention robot system having the X-ray ripple marker 20 attached thereto).

Figure 5A:
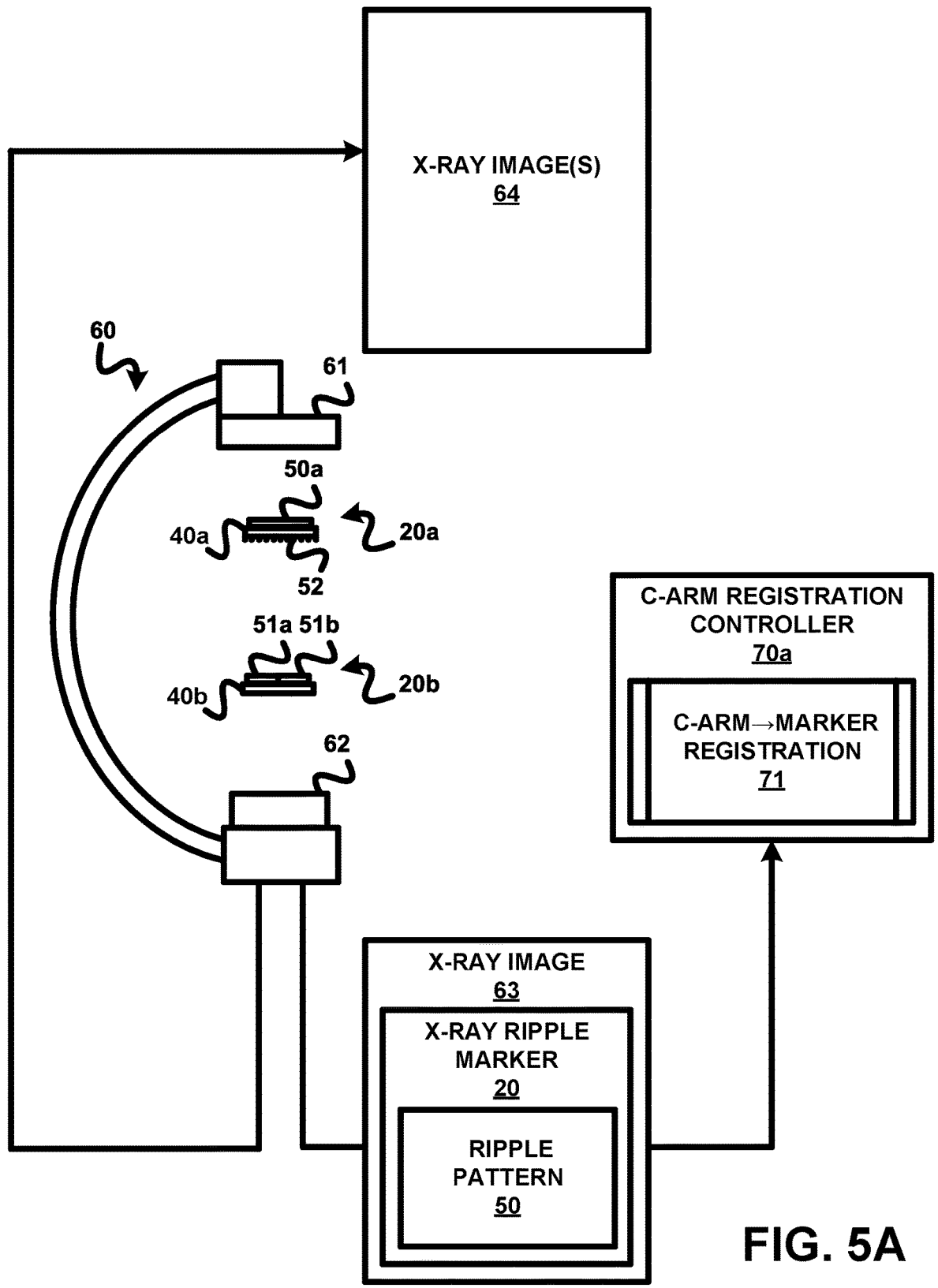
FIG. 5 illustrates an exemplary embodiment of an C-arm registration in accordance with various aspects of the present disclosure.
Figure 5B:
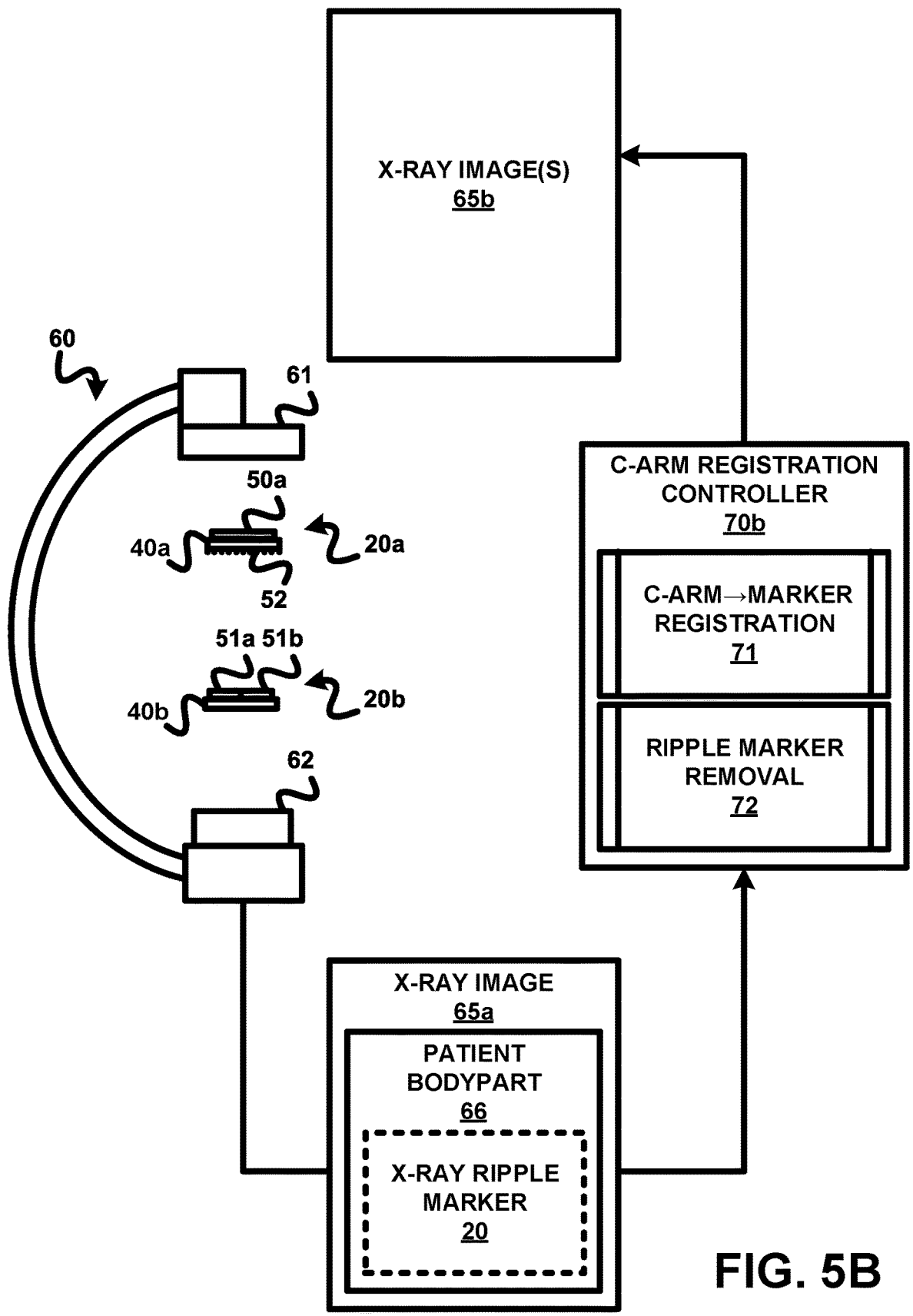

FIG. 7 illustrates a flowchart 80 representative of a C-arm to marker registration 71 executable upon a Referring to FIG. 7, a stage S82 of flowchart 80 encompasses controller 70 identifying a signature and a ripple pattern 50 of X-ray ripple marker 20 in the X-ray image 63 in the patient-less mode of FIG. 5A or in the X-ray image 65a of the patient mode of FIG. 5B. The identification of ripple pattern 50 within the X-ray image is characteristic of a position of the X-ray projection by the C-arm 60 (e.g., focal spot 65) relative to the X-ray ripple marker 20, meaning a location and/or an orientation the X-ray projection within coordinate system 21 or coordinate system 22 is characterized by ripple pattern 50 as illustrated within the X-ray image.

In practice, knowing the geometry of X-ray ripple marker 20 may serve as a basis for identifying X-ray maker 20 within the X-ray image when an entirety of X-ray ripple marker 20 is illustrated within the X-ray image, or the utilization of a landmark pattern (e.g., landmark pattern of copper balls 53) may serve as a basis for identifying X-ray maker 20 within the X-ray image when a portion of X-ray ripple marker 20 is illustrated within the X-ray image.

For example, in the patient-less mode, X-ray ripple marker 20 may be aligned between focal spot 65 and X-ray detector 62 whereby an entirety of X-ray ripple marker 20 may be illustrated within X-ray image 63 (FIG. 5A).

By further example, in the patient mode, a landmark pattern of copper balls 53 (FIG. 4D) may be utilized to find the fixed point of X-ray ripple marker 20 (e.g., the center point), particularly when a portion of the X-ray ripple marker 20 is illustrated within X-ray image 65a (FIG. 5B).

A stage S84 of flowchart 80 involves a derivation of transformation parameter(s) from the ripple pattern 50 identified in stage S82 to thereby register X-ray ripple marker 20 and X-ray C-arm 60 during a stage S86 of flowchart 80.

In practice, stage S84 involves a generation of transformation signal(s) from frequency(ies), phase(s) and/or amplitude(s) of the radial ripples of ripple pattern 50 identified in stage 82. The transformation signal(s) may be analyzed during stage S84 to derive transformation parameter(s) that define the position of the X-ray projection by the C-arm 60 (e.g., focal spot 65) relative to the X-ray ripple marker 20, meaning a location and/or an orientation of the X-ray projection within coordinate system 21 or coordinate system 22 may now be determined from the transformation parameter(s) during stage S86.

In one embodiment of stages 84 and 86, particularly for embodiments of ripple pattern 50 having an arrangement of radial ripples of the same frequency, phase and amplitude, a pose of X-ray ripple marker 20 in the C-arm space is described by a rigid body transformation composed of a rotation R and a translation t. The rotation is parameterized using ZXZ Euler angles as in accordance with the following equation [1]:

$$R(\theta_{z1},\theta_x,\theta_{z2})=R_z(\theta_{z1})R_x(\theta_x)R_z(\theta_{z2}) \quad [1]$$

where $R_z(\theta)$ is a rotation around z axis with angle $\theta$.

The translation vector t is composed of elementary displace-ments along axes as shown in the following equation [2]:

$$t(t_x, t_y, t_z) = \begin{pmatrix} t_x \\ t_y \\ t_z \end{pmatrix} \quad [2]$$

Any point $p^{Marker} \in R^3$ in marker space 21 or 22 may be converted in C-arm space (e.g., having focal spot 65 as an origin) in accordance with the following equation [3]:

$$p^{C-arm}=R(\theta^{z1},\theta_x,\theta_{z2})p^{Marker}+t(t_x,t_y,t_z) \quad [3]$$

Similarly, a position of any point in C-arm space-$p^{C-arm}$- can be translated in marker space 21 or 22 in accordance with the following equation [4]:

$$p^{Marker}=R(\theta_{z1},\theta_x,\theta_{z2})^T p^{C-arm} - R(\theta_{z1},\theta_x,\theta_{z2})^T t(t_x,t_y,t_z) \quad [4]$$

In a second embodiment of stages 84 and 86, particularly for embodiments of ripple pattern 50 having an arrangement of a first series radial ripples and a second series of radial ripples having a frequency, a phase and/or an amplitude dissimilar from the first series of radial ripples, a distance from the focal spot 65 to the fixed point of the X-ray ripple marker 20 may be determined from the dissimilar frequencies, dissimilar phases and/or dissimilar amplitudes as will be exemplary described in the present disclosure with the description of FIGS. 13-18B.

Still referring to FIG. 7, for the patient mode only, a stage S88 of flowchart 80 involves a removal of X-ray ripple marker 20 from X-ray image 65a (FIG. 5B) to render X-ray image 65b (FIG. 5B). In practice, any technique may be used to remove the X-ray ripple marker 20 in a manner that minimizes, if not impedes, an induce artifacts and/or affect the illustrates of the patient body part in a same spatial frequency ranges as X-ray ripple marker 20.

In one embodiment, a frequency-based filtering technique may be utilized during stage S88.

In a second embodiment, image subtraction technique may be utilized involving a transformation of a model of X-ray ripple marker 20 to an actual location and orientation of X-ray ripple marker in the X-ray image 65a to thereby subtract the X-ray ripple marker in the X-ray image 65a with minimal effect on image quality as will be exemplary described in the present disclosure with the description of FIGS. 12A-12F.

Figure 8A:
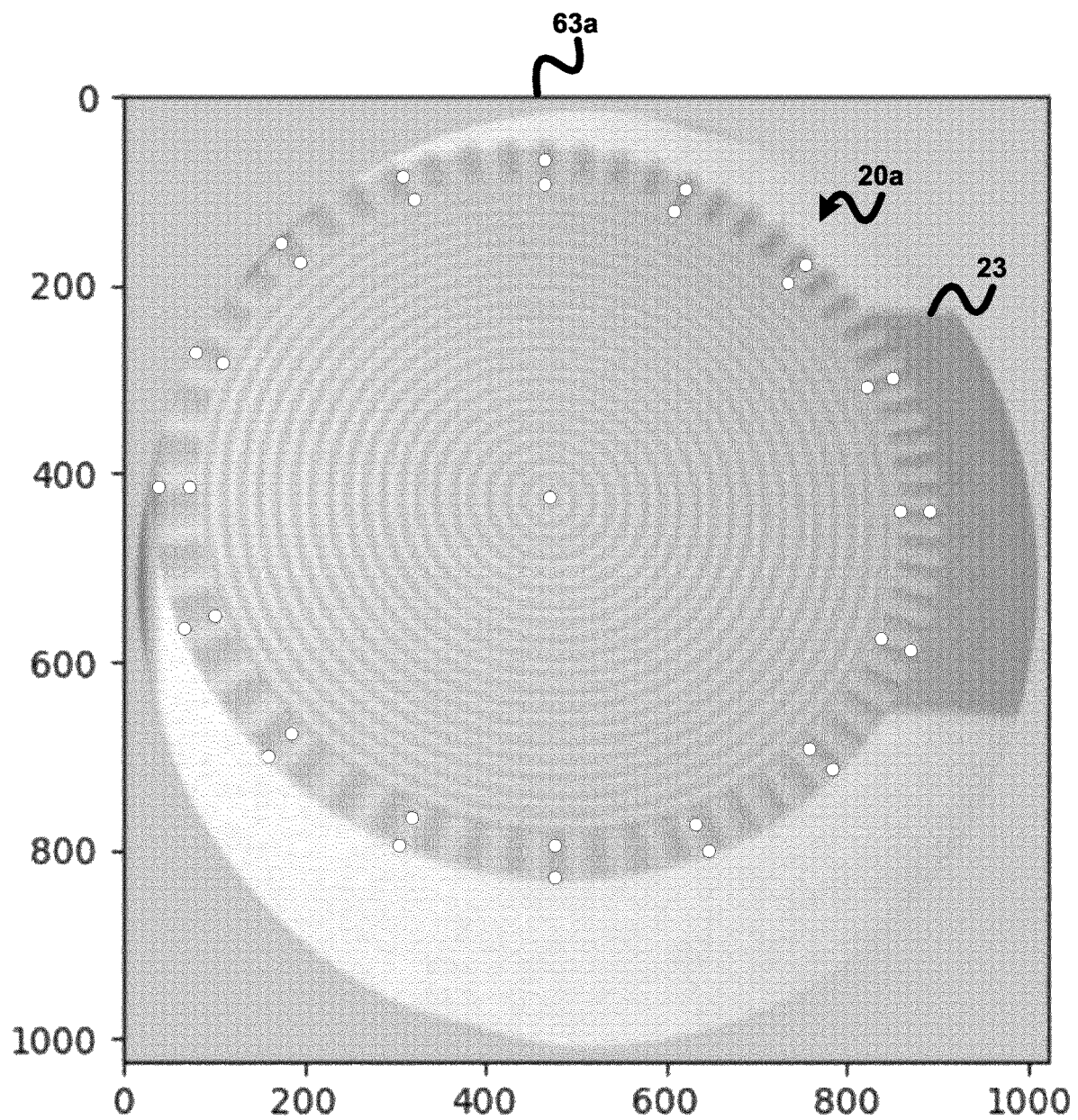
FIGS. 8A and 8B illustrate an exemplary sinusoidal signal transformation in accordance with various aspects of the present disclosure.

The following is a description of one embodiment of a patient mode of C-arm registration controller 70 (FIG. 5B) in the context of an X-ray image 63a of an X-ray ripple marker 20a being held by an arm 23 (e.g., a robot extension or C-arm extension) as shown in FIG. 8A. In practice, where the ripple pattern 50 of X-ray ripple marker 20a is passed through a perspective transformation, the pattern 50 will change into a chirp signal whereby the following equation [5] will become the following equation [6] whereby wave projection parameters $c_1$ and $c_2$ are a function of the perspective transformation parameters:

$$s(r)=A\exp(2\pi i f_m r) \quad [5]$$

$$s_p(r) = A_1 \exp\left(2\pi j f_m \frac{c_1 r}{1+rc_2}\right) \quad [6]$$

where s(r) is the model sinusoidal pattern, A is the amplitude, $f_m$ is the frequency, and $s_p(s)$ is the projective geometry transformed pattern of s(r).

Figure 8B:
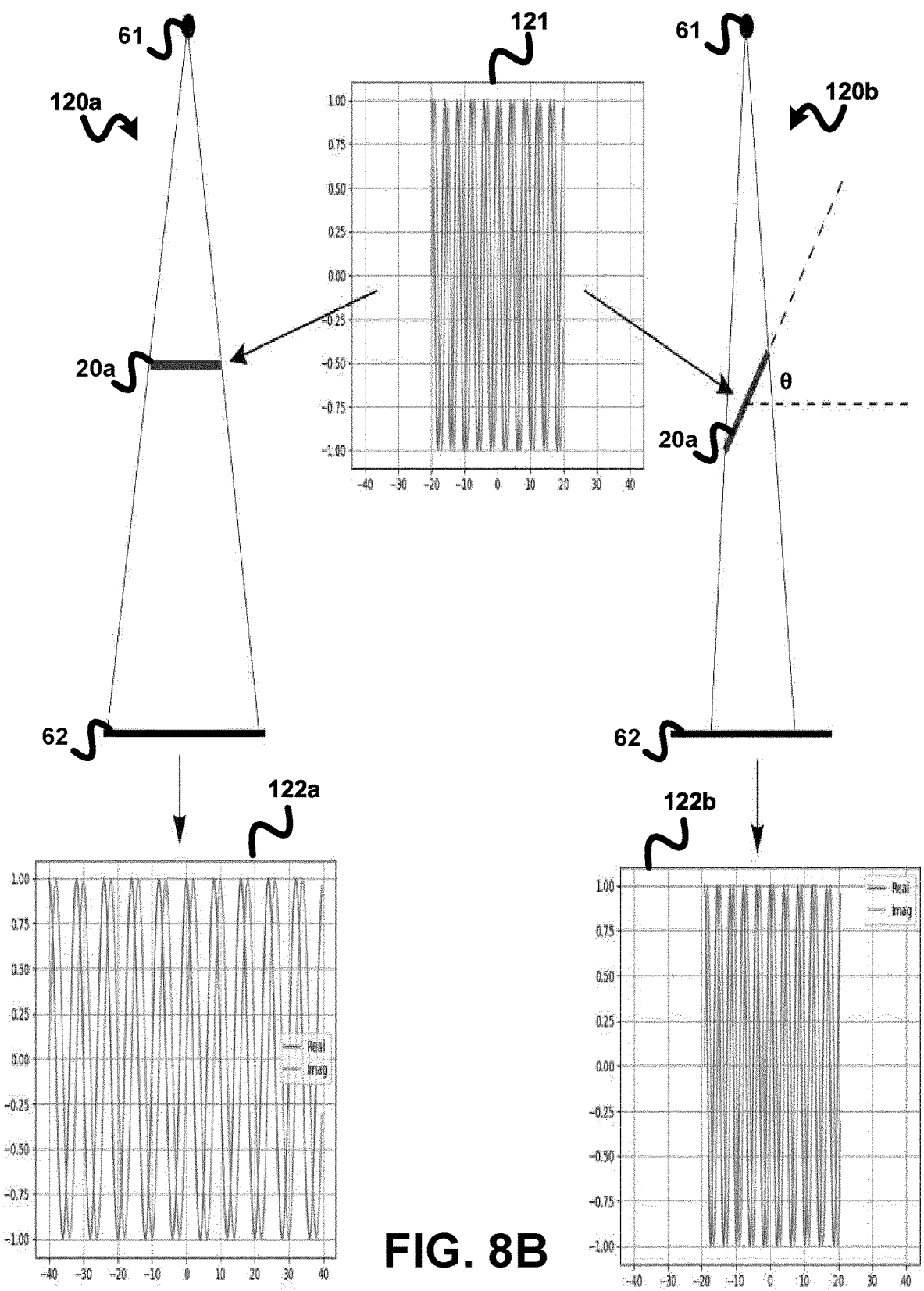

FIG. 8B shows the transformation of the sinusoidal signal of X-ray ripple marker 20 through a perspective projection. If the marker 20 is parallel with X-ray detector 62 and at a midpoint of an X-ray projection 120a as shown, then an original sinusoidal signal 121 of marker 20 is stretched into sinusoidal signal 122a whereby $c_1$=0.5 and $c_2$=0.0. If the marker 20 is tilted with respect to X-ray detector 62 and at a midpoint of an X-ray projection 120b as shown, the $c_2$>0, resulting in a chirp signal 122b (e.g., $c_1$=1.0 and $c_2$=0.002). Thus, the signal along each diagonal of the marker is transformed through the perspective transformation into wave projection parameters $c_1$ and $c_2$.

Figure 9:
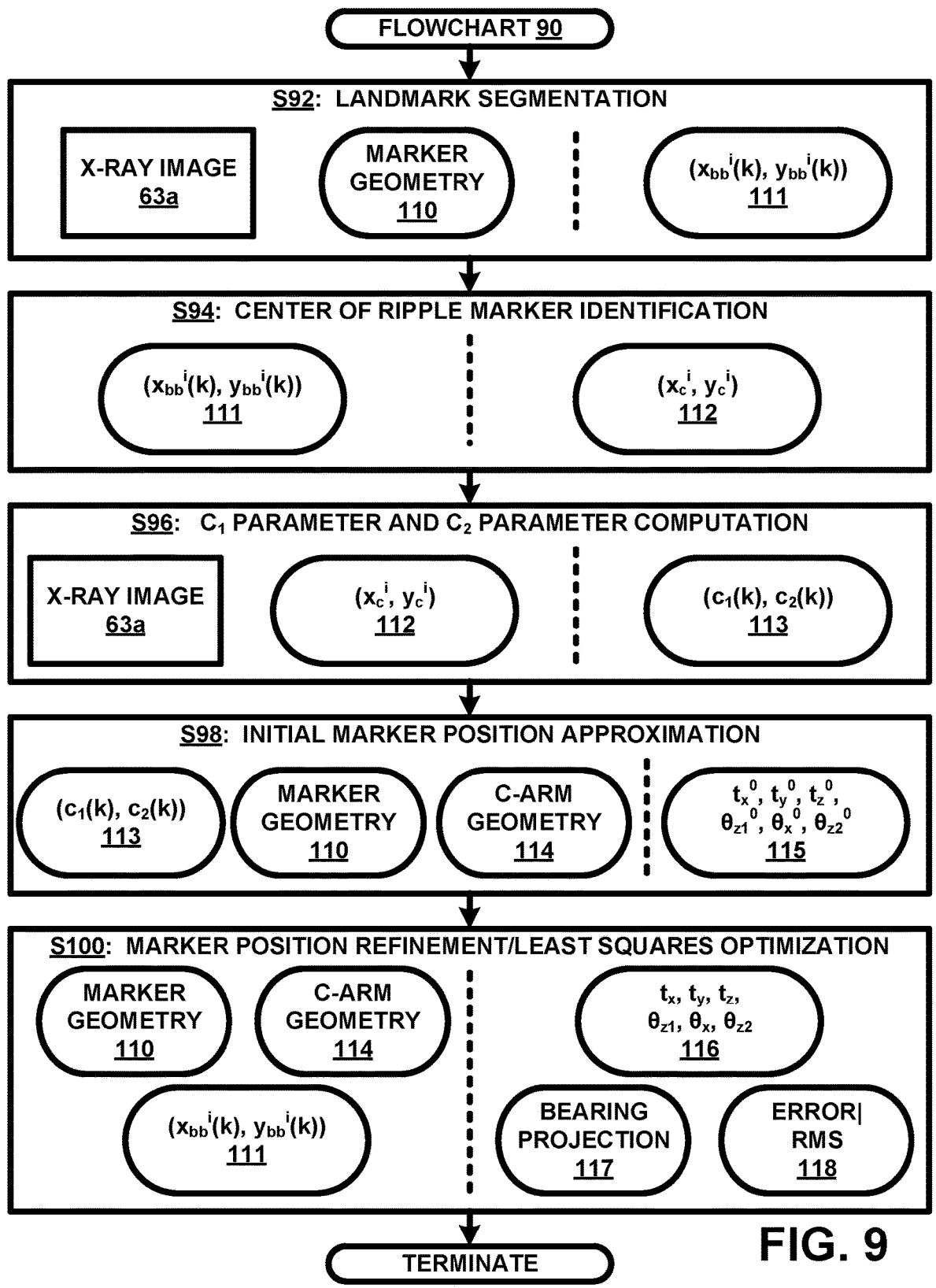
FIG. 9 illustrates a flowchart representative of a first exemplary embodiment of transformation parameter generation method in accordance with various aspects of the present disclosure.

FIG. 9 illustrates a flowchart 90 representative of a transformation generation method for X-ray ripple marker 20a shown in FIG. 8A.

Referring to FIG. 9, a stage S92 of flowchart 90 encompasses controller 70 processing an acquired X-ray image 63a and a stored marker geometry 110 to compute ($x_{bb}^i(k)$, $y_{bb}^i(k)$) coordinates 111 for each ball bearing landmark of X-ray ripple marker 20a to thereby find ($x_c^i$, $y_c^i$) coordinates 112 for the center point of X-ray ripple marker 20a during a stage S94 of flowchart 90.

A stage S96 of flowchart 90 encompasses controller 70 processing acquired X-ray image 63a and computed center point ($x_c^i$, $y_c^i$) coordinates 112 to compute wave projection parameters $c_1$ and $c_2$.

A stage S98 of flowchart 90 encompasses controller 70 processing acquired X-ray image 63a, wave projection parameters $c_1$ and $c_2$ and stored marker geometry 110 and C-arm geometry to obtain an initial approximation of transformation parameters ($t_x^0$, $t_y^0$, $t_z^0$, $\Theta_x^0$, $\Theta_y^0$, $\Theta_z^0$) 115.

A stage S100 of flowchart 90 encompasses controller 70 processing transformation parameters ($t_x^0$, $t_y^0$, $t_z^0$, $\Theta_x^0$, $\Theta_y^0$, $\Theta_z^0$)115, ($x_{bb}^i(k)$, $y_{bb}^i(k)$) coordinates 111 for each ball bearing landmark and stored marker geometry 110 and C-arm geometry to obtain a refinement/least square optimization of transformation parameters ($t_x^0$, $t_y^0$, $t_z^0$, $\Theta_x^0$, $\Theta_y^0$, $\Theta_z^0$) 116, bearing projection 117 and error/rms 118.

Figure 10A:
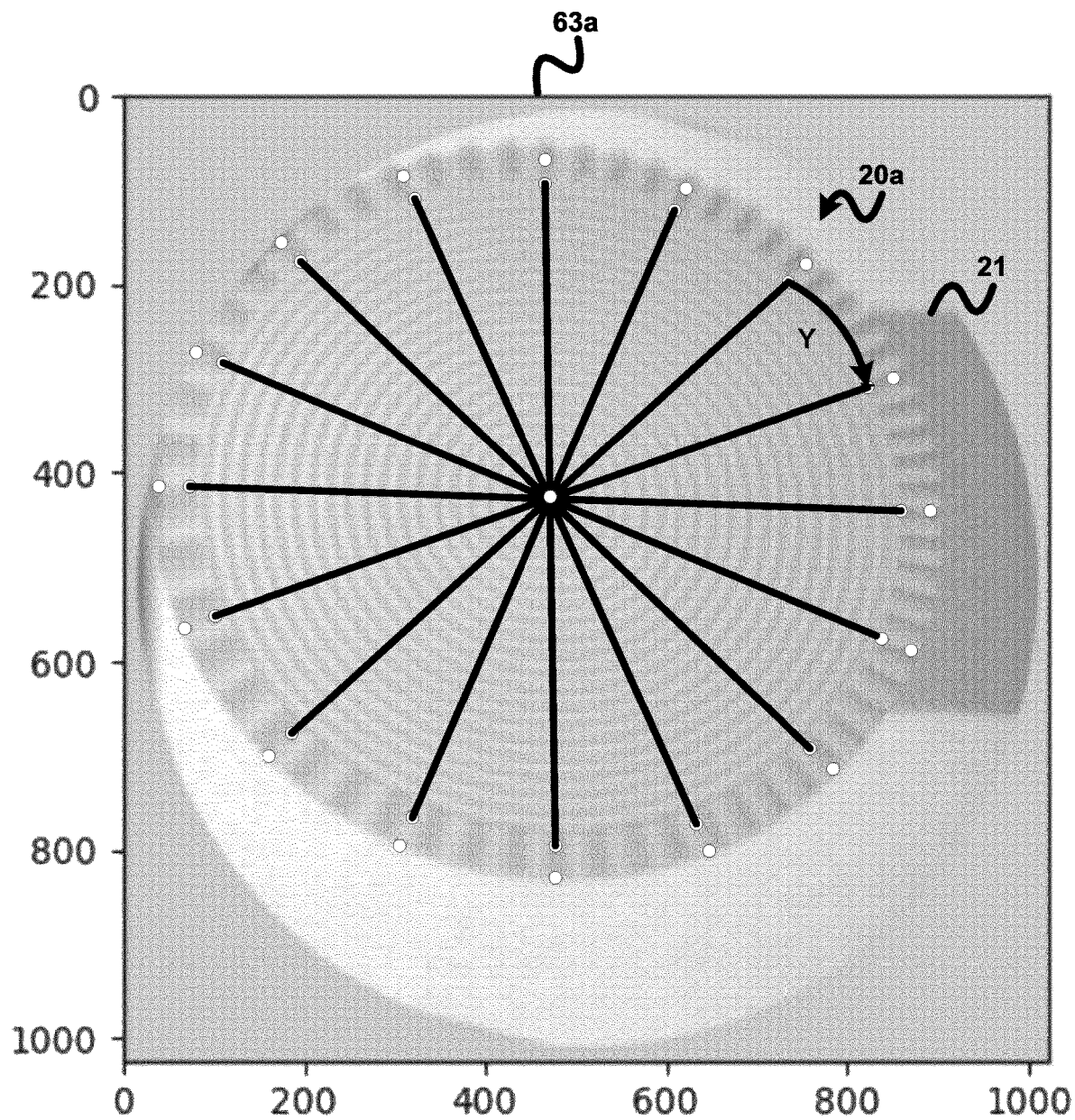
FIGS. 10A-10E illustrate an exemplary transformation parameter generation of FIG. 9 in accordance with various aspects of the present disclosure.

More particularly, in one embodiment of stages S92 and S94, a marker geometry 110 is such that a connection of the closet two (2) ball bearings defines lines that will intersect in the marker center as shown in FIG. 10A. Therefore, the projection of center of X-ray ripple marker 20*a* is identified by segmenting the BBs in the image 63*a* and grouping them to define rays as shown in FIG. 10A. The intersection of these rays defines the center of X-ray ripple marker 20*a* in image space.

The center of the ball bearings is computed using simple thresholding or more advanced algorithms, such as, for example, adaptive thresholding or Otsu thresholding. The ball bearing pairs are formed by simple clustering since the radial neighbor which is of interest is much closer than the lateral ones. After segmentation, blobs that are too small or too large are filtered out. Then, the intersection of the rays is computed using a linear least squares approach.

Figure 10B:
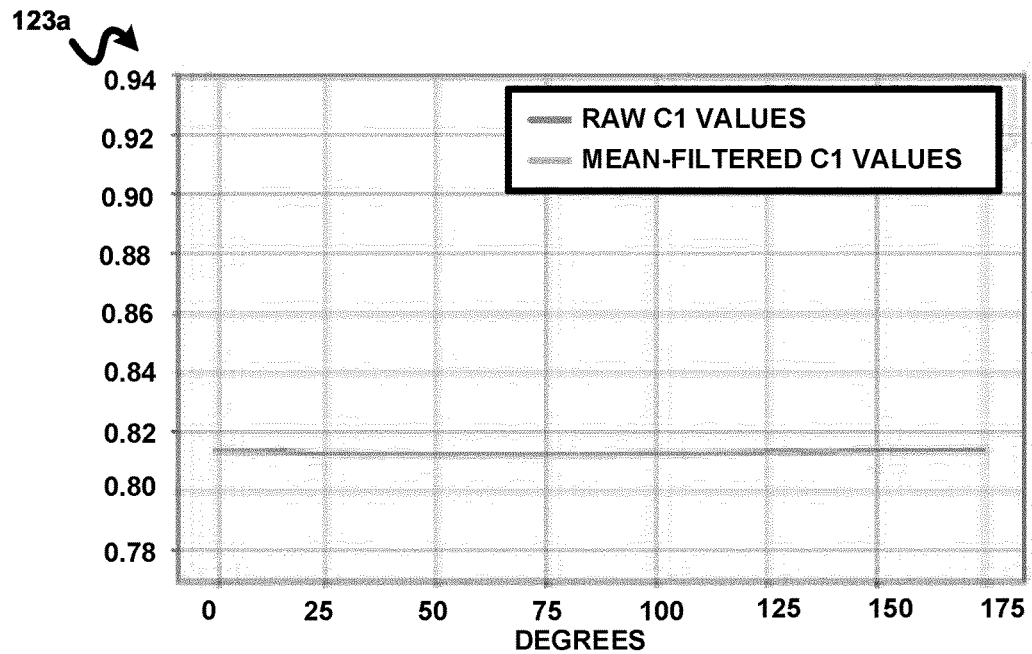
Figure 10C:
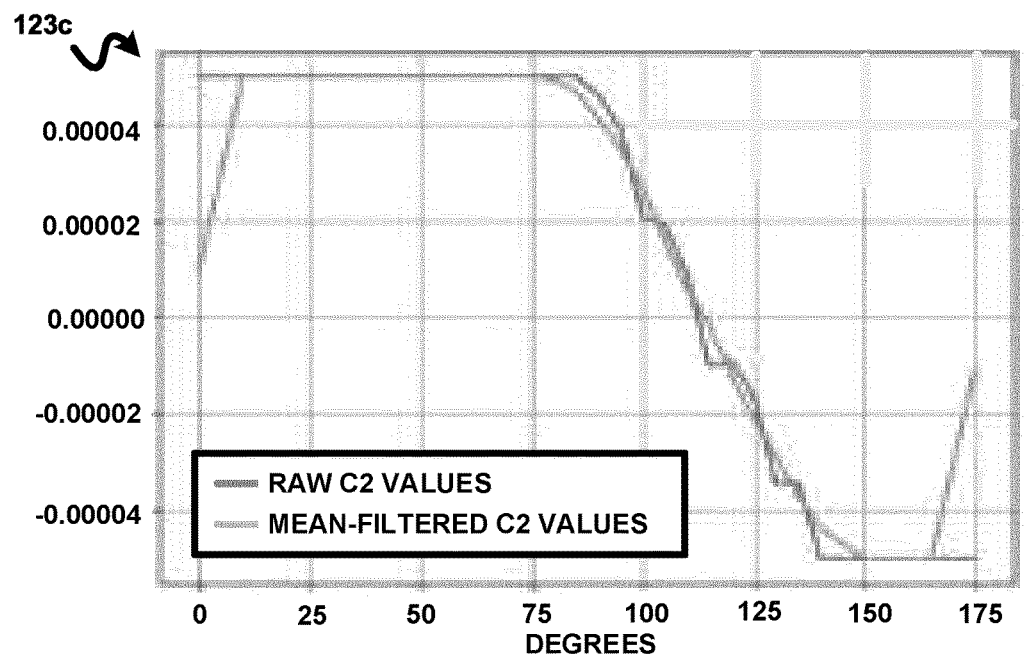
Figure 10D:
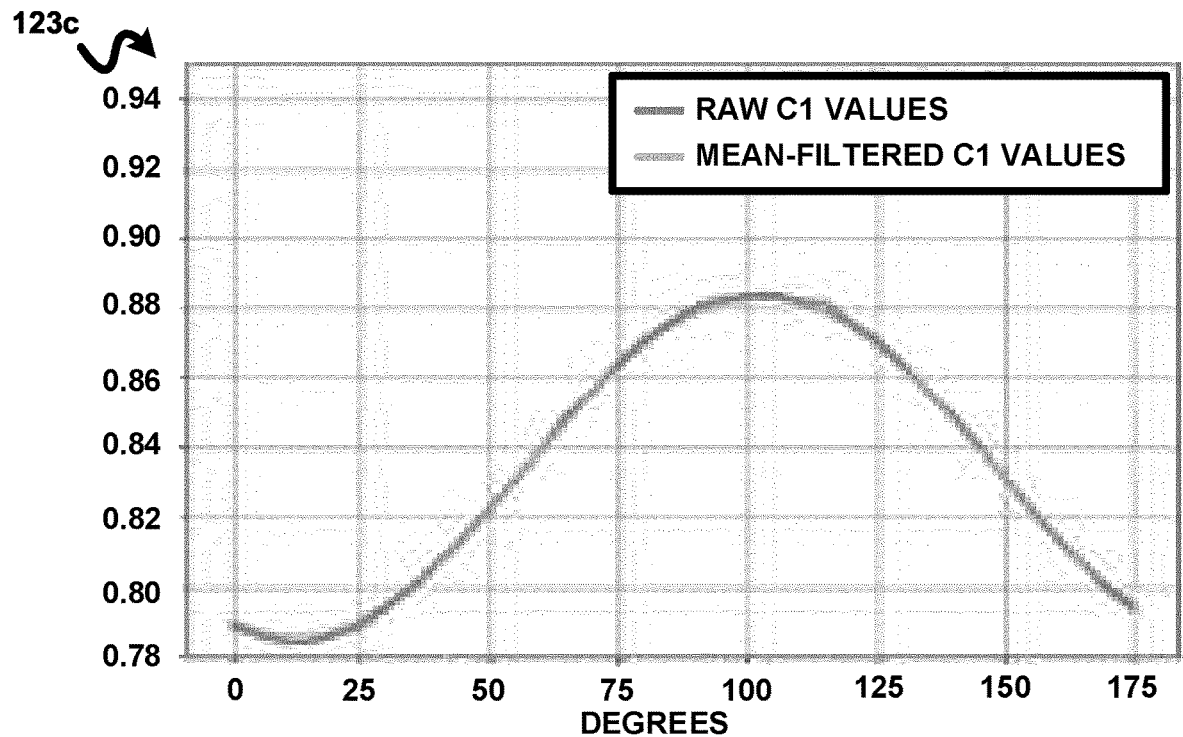
Figure 10E:
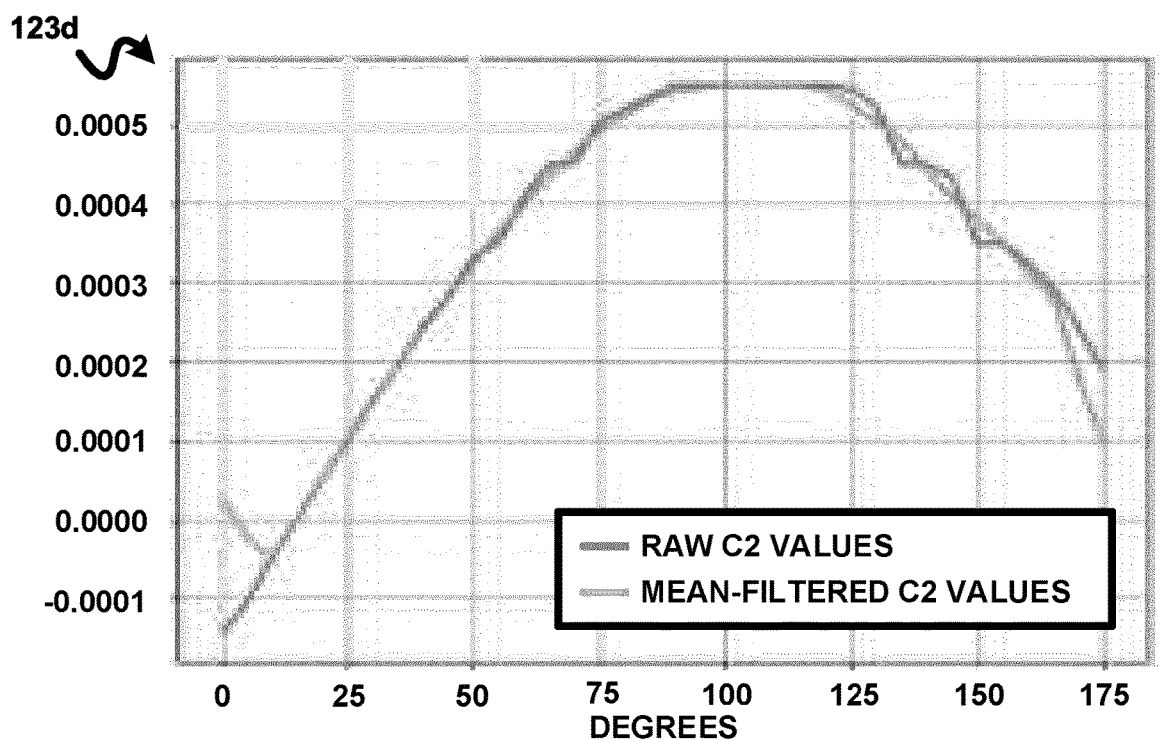

In one embodiment of stage S96, FIG. 10A illustrates a plot 123*a* of wave projection parameter $c_1$ and FIG. 10B illustrates a plot 123*b* of wave projection parameter $c_2$ for two marker positions for X-ray ripple marker 20*a* being parallel with X-ray detector 62 and at a midpoint of an X-ray projection 120*a* as shown in FIG. 8B. FIG. 10C illustrates a plot 123*c* of wave projection parameter $c_1$ and FIG. 10D illustrates a plot 123*d* of wave projection parameter $c_2$ for X-ray ripple marker 20*a* is tilted with respect to X-ray detector 62 and at a midpoint of an X-ray projection 120*b* as shown in FIG. 8B. The computation of wave projection parameters $c_1$ and $c_2$ for a diagonal is performed by maximizing the convolution of the image signal along that diagonal with the chirp signal windowed with a Gaussian function.

In one embodiment of stage S98, $c_1$, $c_2$, and arrange of $\gamma$ values are then used to compute the position of X-ray ripple marker 20*a* down to the twist around the axis of the marker 20*a*. An initial approximation of the marker position in the image space comprises five (5) degrees of freedom computed from wave projection parameters $c_1$ and $c_2$ and (1) degree of freedom which is twisted around z axis angle $\Theta_{z2}$. The angle $\Theta_{z2}$ is the one that maximizes the normalized cross correlation between the image signal retrieved at the coordinates corresponding to the projection of the rim chirp using the 5DOF initial position approximation and $\gamma$ twist angle and the model chirp pattern in accordance with the following equation [7]:

$$\text{Twist}_{chirp}(\gamma) = 40 * \gamma * \left(1.0 + \frac{\gamma}{2*\pi}\right) \quad [7]$$

Figure 11A:
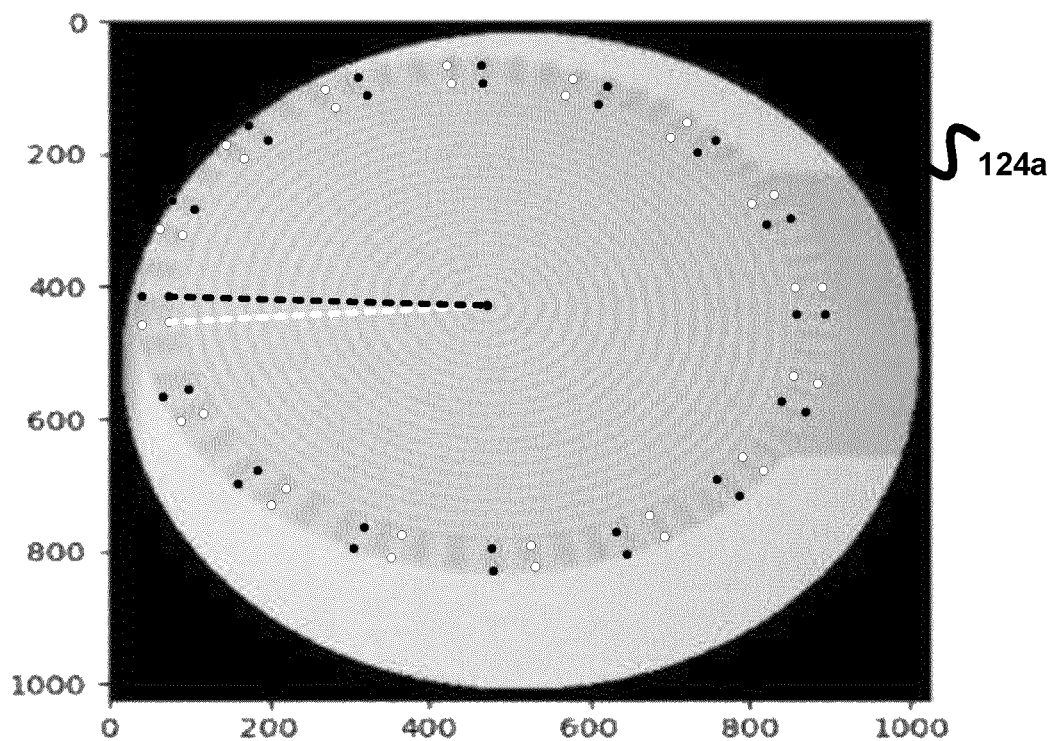
FIGS. 11A and 11B illustrate an exemplary marker position approximation/refinement of FIG. 9 in accordance with various aspects of the present disclosure.
Figure 11A:
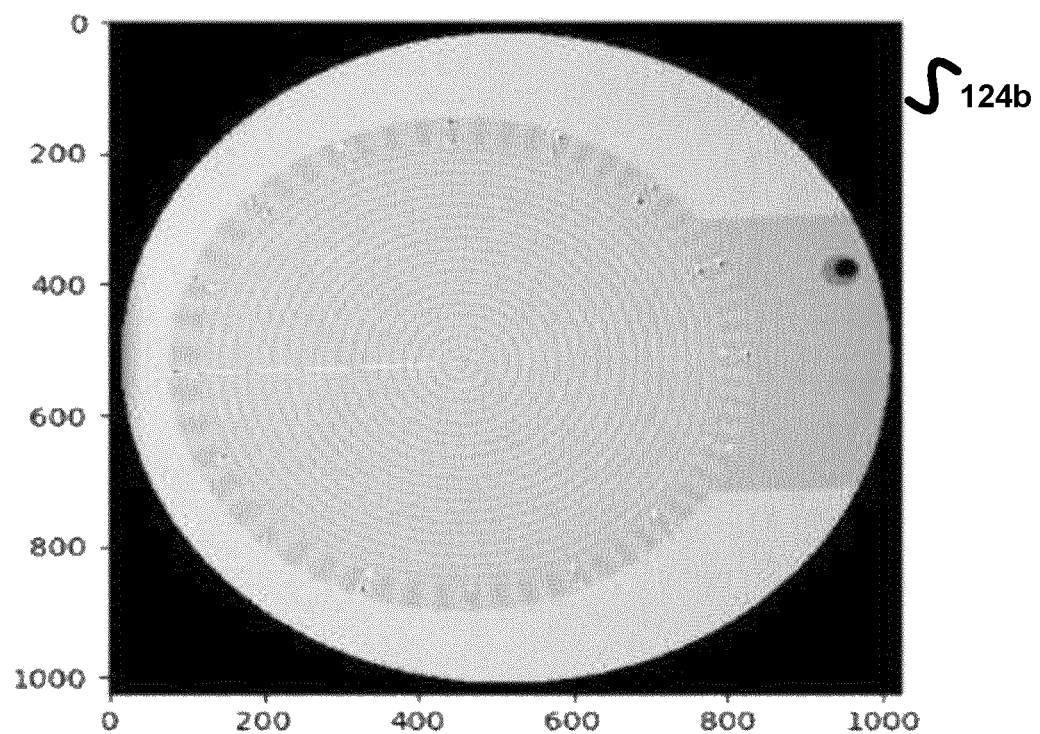

FIG. 11A shows a registration verification after an initial approximation whereby a computed position 124*a* of marker 20*a* is very close to a true position 125*b* of marker 20*a* due to an error in the twist.

In one embodiment of stage S100, the computed position is optimized using a least squares approach. For each ball bearing identified in the image, $b_i$; i=1 ... n, a model corresponding to position $b'''i$; i=1 ... n is computed and subsequently, using the approximate parameters $t_x$, $t_y$, $t_z$, $\theta_{z1}$, $\theta_x$, $\theta_{z2}$ and C-arm geometry 115, virtual projections are computed in accordance with the following equations [8] and [9]:

$$b_i^{C-arm} = R_Z(\theta_{Z1})R_Z(\theta_x)R_Z(\theta_{Z2})b_i^m + (t_x t_y t_z)^T \equiv \begin{pmatrix} bx_i^{C-arm} \\ by_i^{C-arm} \\ bz_i^{C-arm} \end{pmatrix} \quad [8]$$

$i = 1 \ldots n$ $$\tilde{b}_i = \begin{pmatrix} psz_x^* & x_s \\ psz_y^* & y_s \end{pmatrix} + \frac{z_S}{z_s - bz_-^{C-arm}} * \begin{pmatrix} psz_x^* & bx_i^{C-arm} \\ psz_y^* & by_i^{C-arm} \end{pmatrix}; \quad [9]$$

$i = 1 \ldots n$ where $(x_s, y_s, z_s)^T$ is the position of the source 61 with respect to the detector 62 coordinate system, and $psz_x$ and $psz_y$ are the pixel sizes in x and y directions. It is assumed that the detector coordinate system coincides with the image coordinate system with only a difference in pixel size.

A cost function may then represented in accordance with the following equation [10]:

$$C(t_x,t_y,t_z,\theta_{z1},\theta_x,t\theta_{z2})=\Sigma_{i-1}^n\|b_i-\tilde{b}_i\|_2^2 \quad [10]$$

The cost function is minimized using a "Nelder-Mead" algorithm.

Figure 11B:
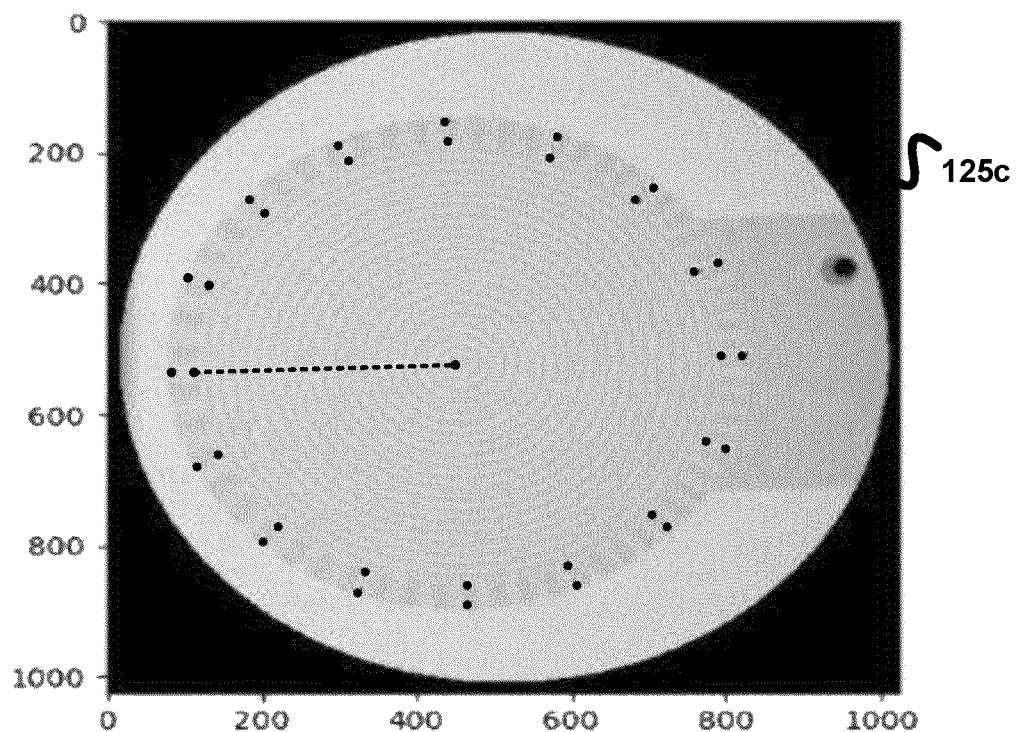
Figure 11B:
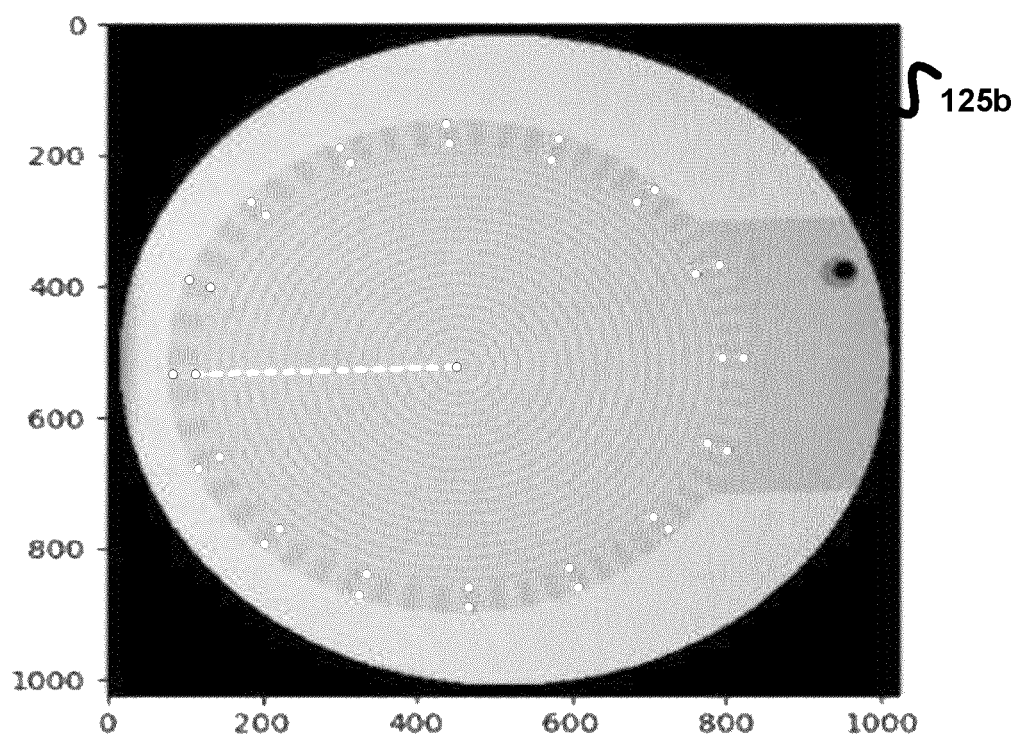

FIG. 11B shows a registration verification after final optimization whereby a computed position 124*c* of marker 20*a* corresponds to true position 125*b* of marker 20*a*.

Figure 12A:
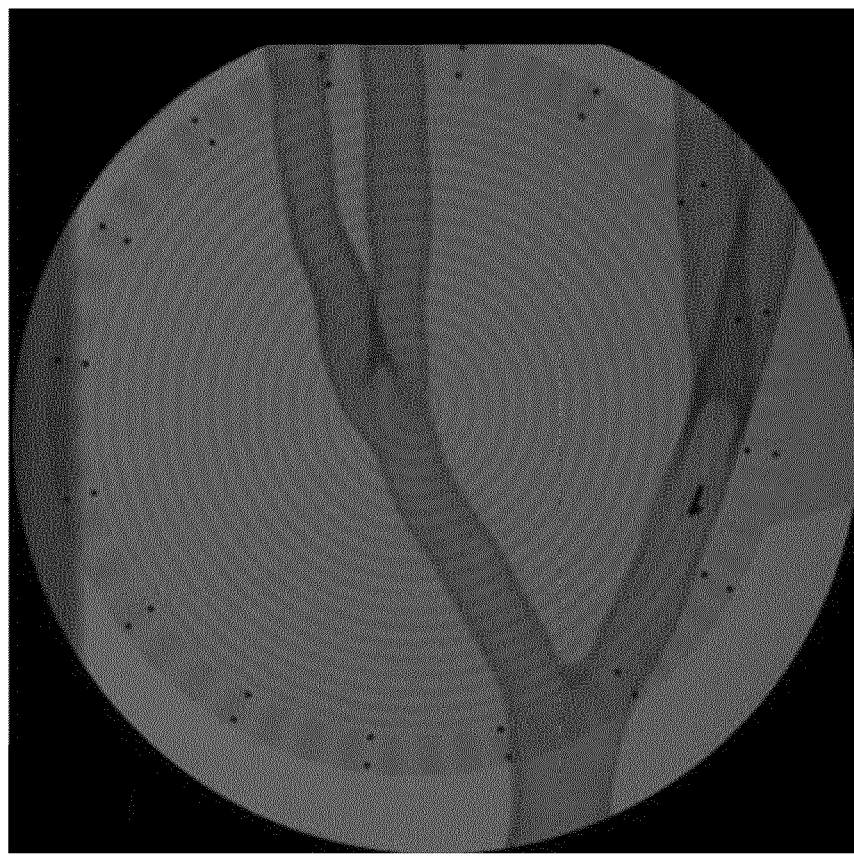
FIGS. 12A-12F illustrate an exemplary X-ray ripple marker image subtraction of FIG. 7 in accordance with various aspects of the present disclosure.
Figure 12B:
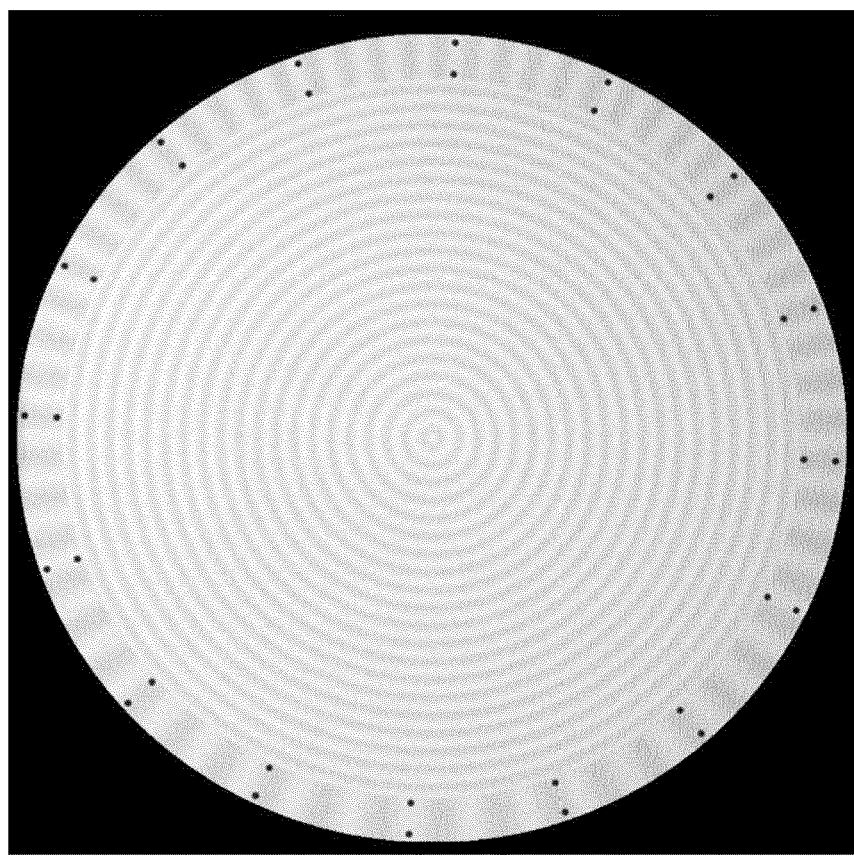
Figure 12C:
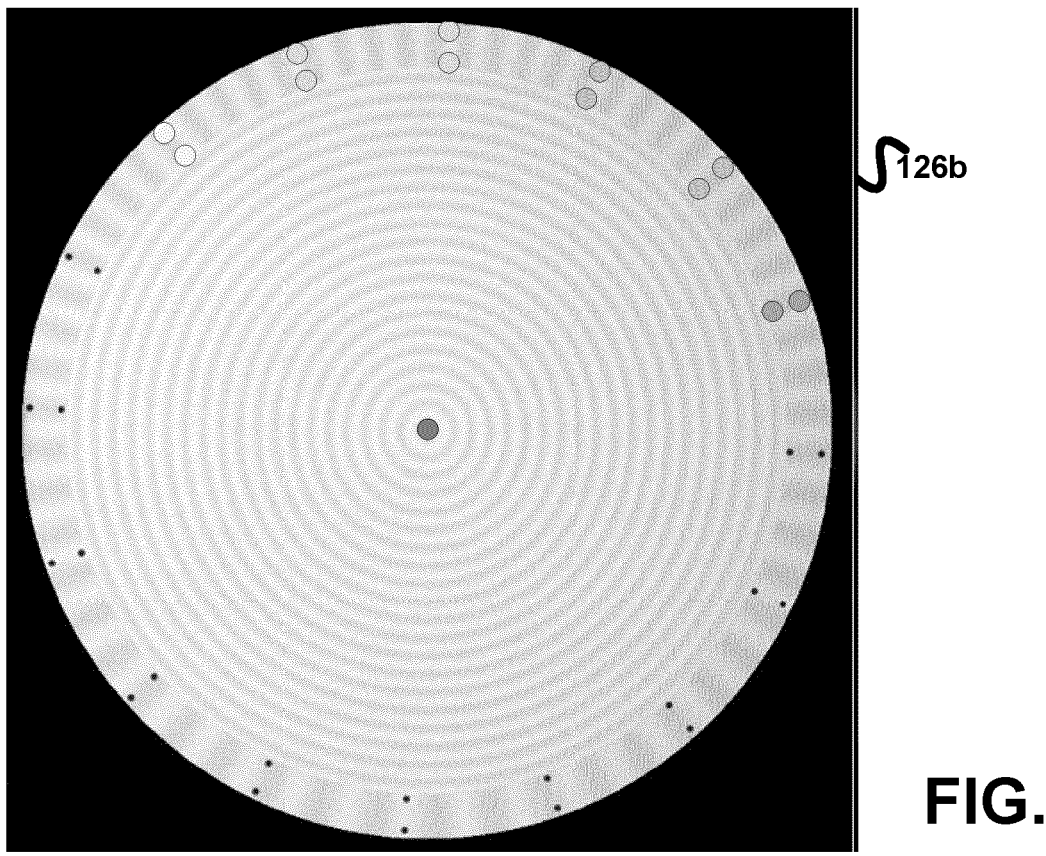

Referring to FIG. 7, a subtraction embodiment of stage S88 for a patient image 65*a* of X-ripple marker 20*a* as shown in FIG. 12A utilizes a pre-acquired image 126*a* of X-ray image marker 20*a* alone in the field of view as shown in FIG. 12B, which will be referred to as the marker model. Additional interventional images can then be acquired that contain all or part of the marker at a variety of orientations. The marker model 20*a* is matched toan interventional image (e.g., interventional image 65*a*) using a point-to-point homographic transform based on the location of the ball bearings (for example, in OpenCV: cv2.findHomography ((Pts$_{model}$),(Pts$_{image}$))). Ball bearings were used for the point-to-point transform in this case because ball bearings are clear fiducials in each image, although any other points on the marker could be used instead of the ball bearings. In order to match the correct corresponding pairs of ball bearings in the marker model 126*a* with those in the interventional image 65*a*, the ball bearings are detected in order radially starting from the x-axis of the marker model 126*b* as shown in FIG. 12C.

Figure 12D:
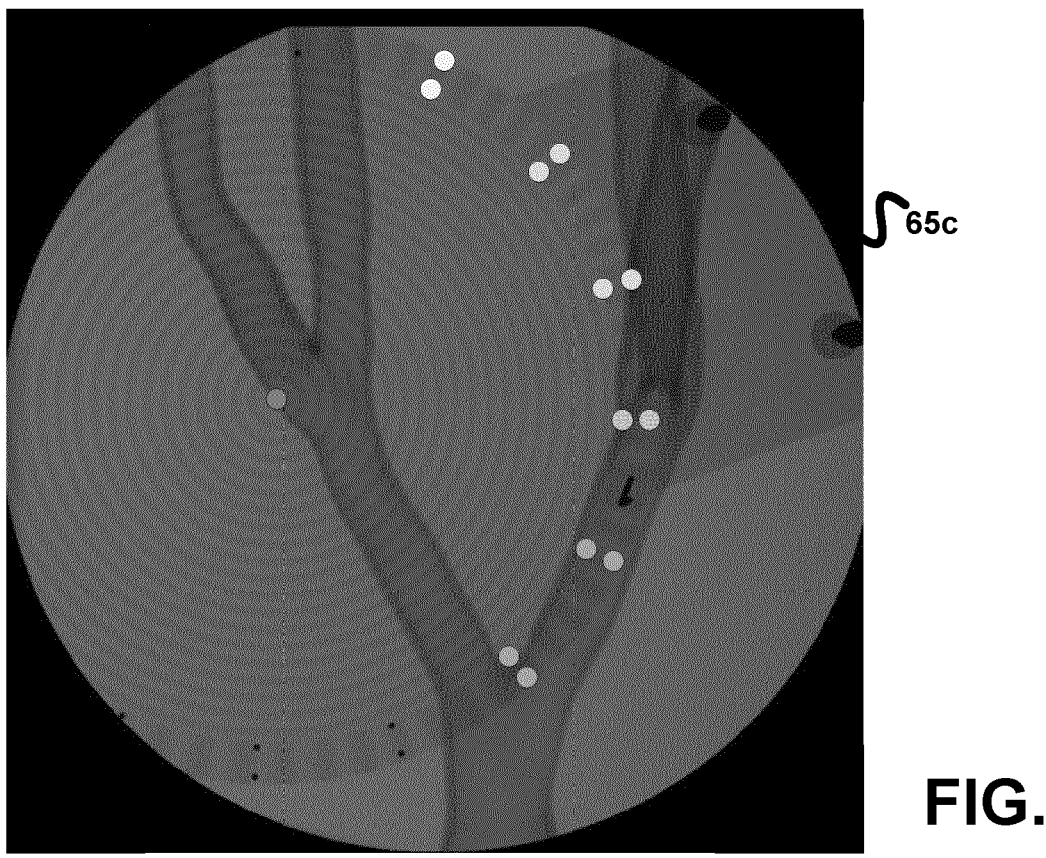
Figure 12E:
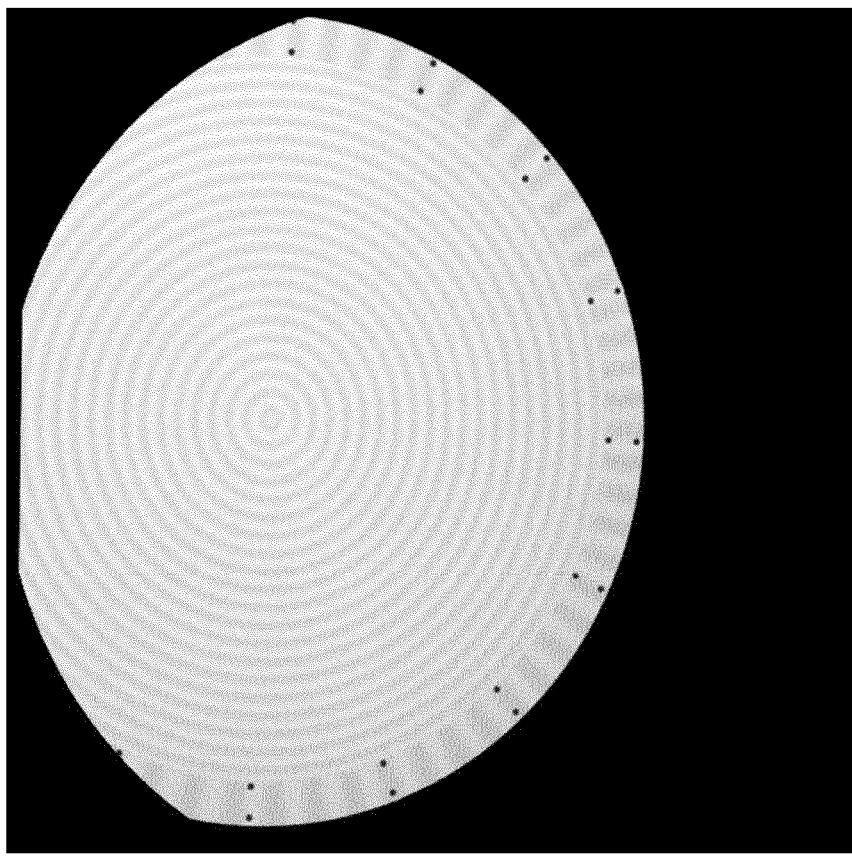
Figure 12F:

Once the point-to-point homographic transform has been applied to the marker model 126*b* to provide a rough registration 65*c* of FIG. 12D to the interventional marker in image space, the model alignment is fine-tuned using an enhanced correlation coefficient (ECC) optimization routine (e.g., iOpenCV:cv2.findTransformECC( ). Once optimal alignment between the marker model 126*b* and the image has been achieved, the aligned marker model 126*c* as shown in FIG. 12E is subtracted from the image to render image 65*d* of FIG. 12F, where the gray level of the subtracted model is optimized based on minimizing the power of the main frequency of the marker in the image. A uniform offset representing the mean gray level of the subtracted marker is added back into the image in the marker region.

The following Table I outlines the subtraction techniques

TABLE 1

Subtraction Technique

1: Compute model location in image space (Model)
2: Compute marker location in image space (Image)
3: Locate equivalent fiducial points in the model ($Pts_{image}$) and the image ($Pts_{model}$)
4: Compute point-to-point homographic transform ($Pts_{image} = T_{homography} * Pts_{model}$)
5: Transform model into marker space ($Model_{transformed} = T_{homography} * Model$)
6: Compute fine-tuned transformation ($T_{correlation}$) by optimizing image correlation
7: Make final model transform ($Model_{fineTuned} = T_{correlation} * Model_{transformed}$)
8: Subtract final model from image ($Image_{subtracted} = Image - Model_{finetuned}$)
9: Add mean value offset to subtracted marker region ($Image_{final} = Image_{subtracted} - Model_{mean}$)

Figure 14:
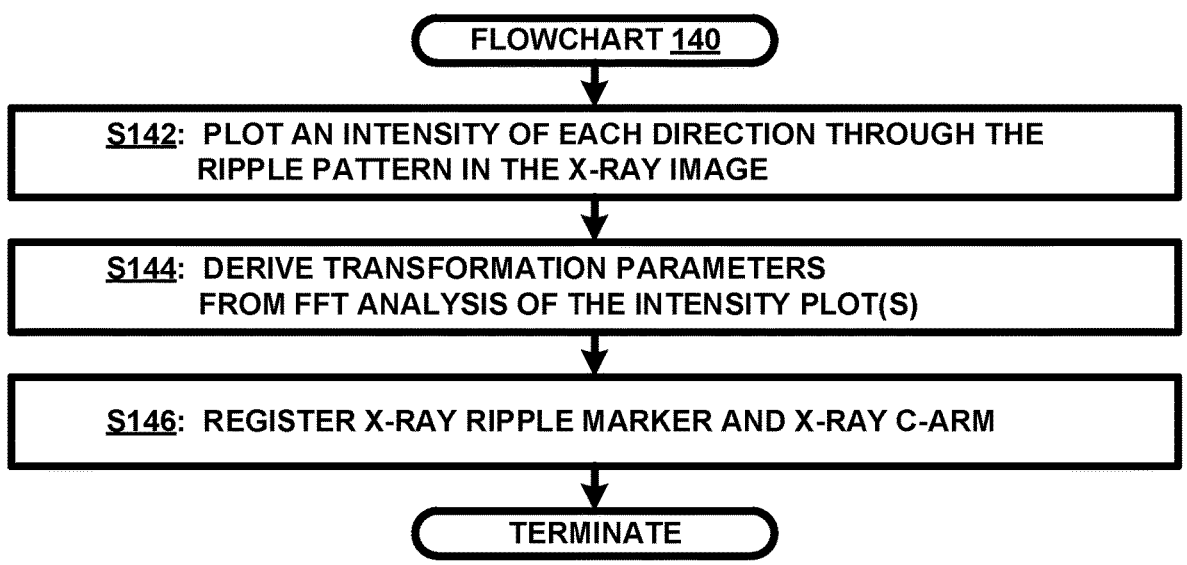
FIG. 14 illustrates a flowchart representative of a second exemplary embodiment of an C-arm registration of FIG. 5 in accordance with various aspects of the present disclosure.
Figure 15A:
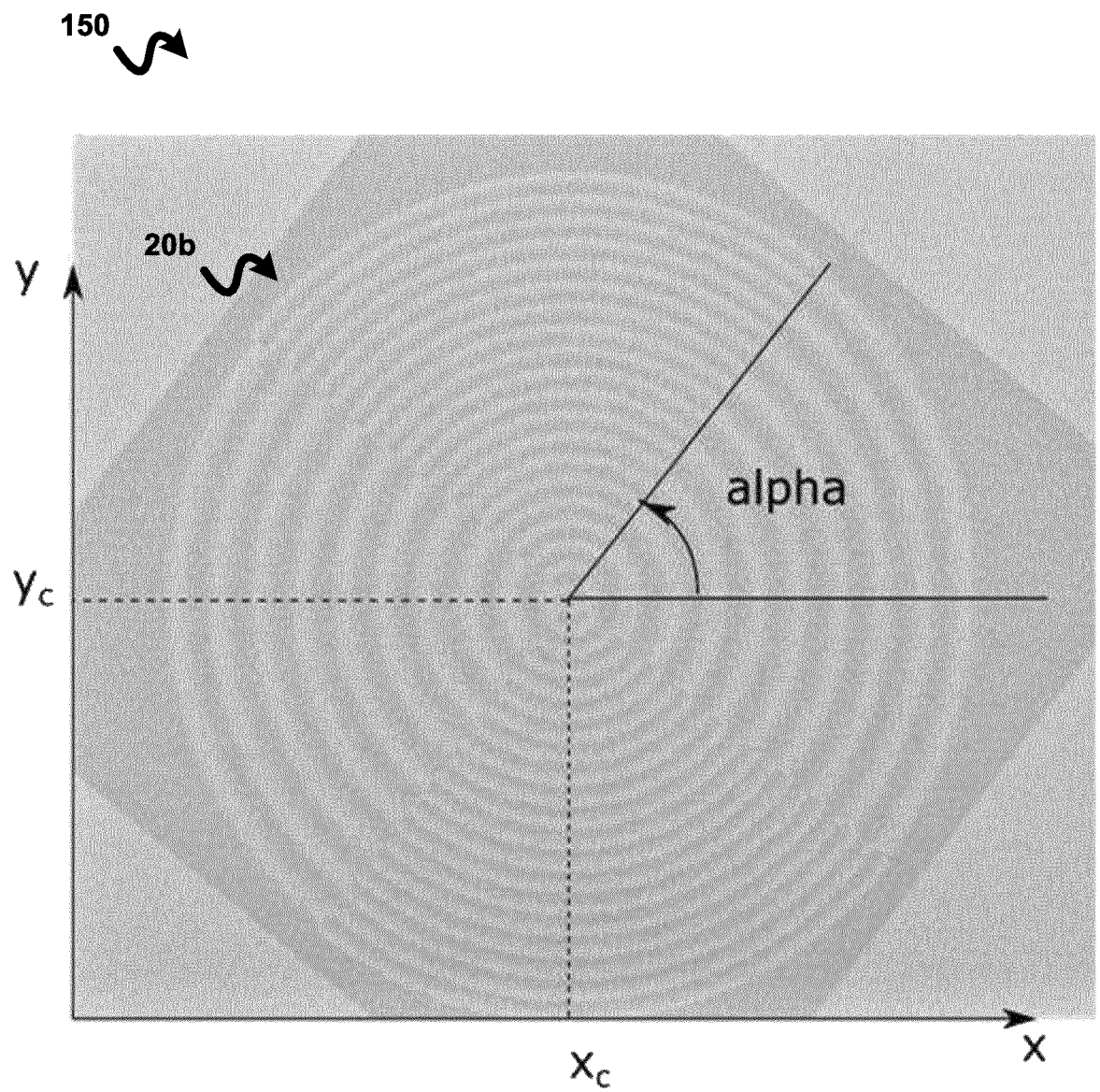
FIGS. 15A and 15B illustrate an exemplary C-arm registration in accordance with various aspects of the present disclosure.

FIG. 14 illustrates a flowchart 140 representative of a transformation generation method for X-ray ripple marker 20*b* shown in FIG. 15A.

Figure 13:
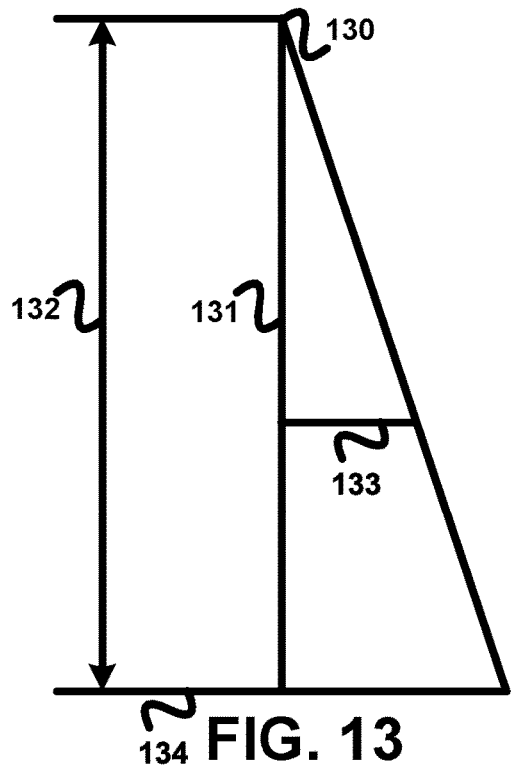
FIG. 13 illustrates an exemplary embodiment of the X-ray projection by a C-arm of FIG. 6 in accordance with the various aspects of the present disclosure.

More particularly to both the patient-less mode and the patient mode, as shown in FIG. 13, the C-arm to marker registration 71 involves projecting one period projecting through the perspective transformation of a distance 132 of an X-ray source 130 to an X-ray detector 134 into a distance 131 of X-ray source 130 to an X-ray ripple marker 133 in accordance with the following equation [11 a]:

$$SM = SD\frac{T_M}{T_I} \quad [11a]$$

where SM is the distance 132 from X-ray source 130 to X-ray ripple marker 133, SD is the distance from X-ray source 130 to X-ray detector 134 (which is known from calibration or DICOM data), $T_M$ is the time period of the ripple pattern and $T_I$ is image period (computed from image). Converting equation [11A] to frequencies yields the following equation [11b]:

$$SM = SD\frac{f_I}{f_M} \quad [11b]$$

$f_M$ is the frequency of the known ripple pattern and $f_I$ is image frequency (computed from image).

Equation [11b] is for looking in one direction of the image. The following equation [11c] is for two directions suitable for X-ripple marker 20*b* (FIG. 15A):

$$SM = SD\left(\frac{f_H^I}{f_H^M} + \frac{f_L^I}{f_L^M}\right) \quad [11c]$$

where $f_H^M$ is the highest frequency of the known ripple pattern, $f_L^M$ is the highest frequency of the known ripple pattern, $f_H^I$ is highest image frequency (computed from image) and $f_L^I$ is lowest image frequency (computed from image).

In practice, more than two directions may be utilized. Also in practice, a simplest approach is by using fast Fourier transform (FFT) along lines going through the center of X-ray ripple marker 20*b* of FIG. 15A.

Referring to FIG. 4, a stage S142 of flowchart 140 encompasses controller 70 plotting an intensity of each direction through the ripple pattern of X-ray ripple marker 20*b*, and a stage S144 of flowchart 140 encompasses controller 70 deriving transformation parameter(s) from a FFT analysis of the intensity plot(s).

Figure 16A:
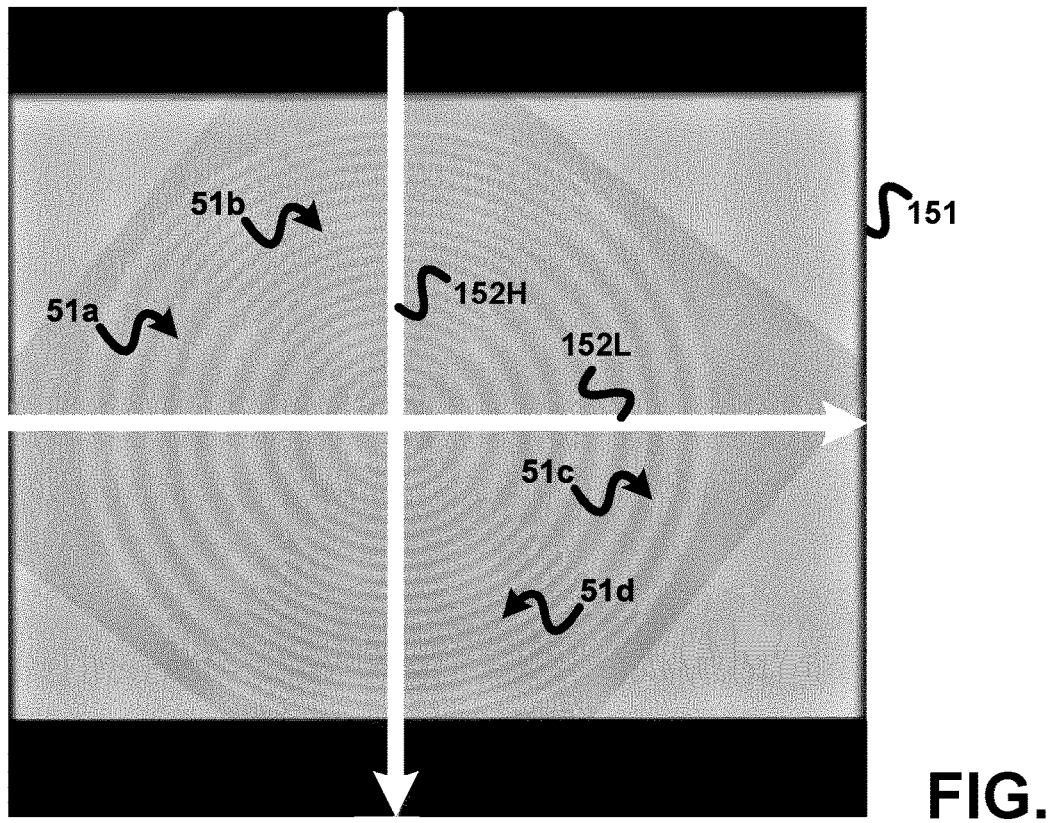
FIGS. 16A and 16B illustrate an exemplary transformation parameter generation of an X-ray ripple marker of FIG. 15A in a first position in accordance with various aspects of the present disclosure.

For example, FIG. 16A illustrates a scenario where the ripple pattern of X-ray ripple marker 20*b* is parallel with the X-ray detector at a first parallel position 151 with a line 152L traversing through low frequency radial ripple series 51*a* and low frequency radial ripple series 51*c*, and a line 152H traversing through high frequency radial ripple series 51*b* and high frequency radial ripple series 51*d*.

Figure 17A:
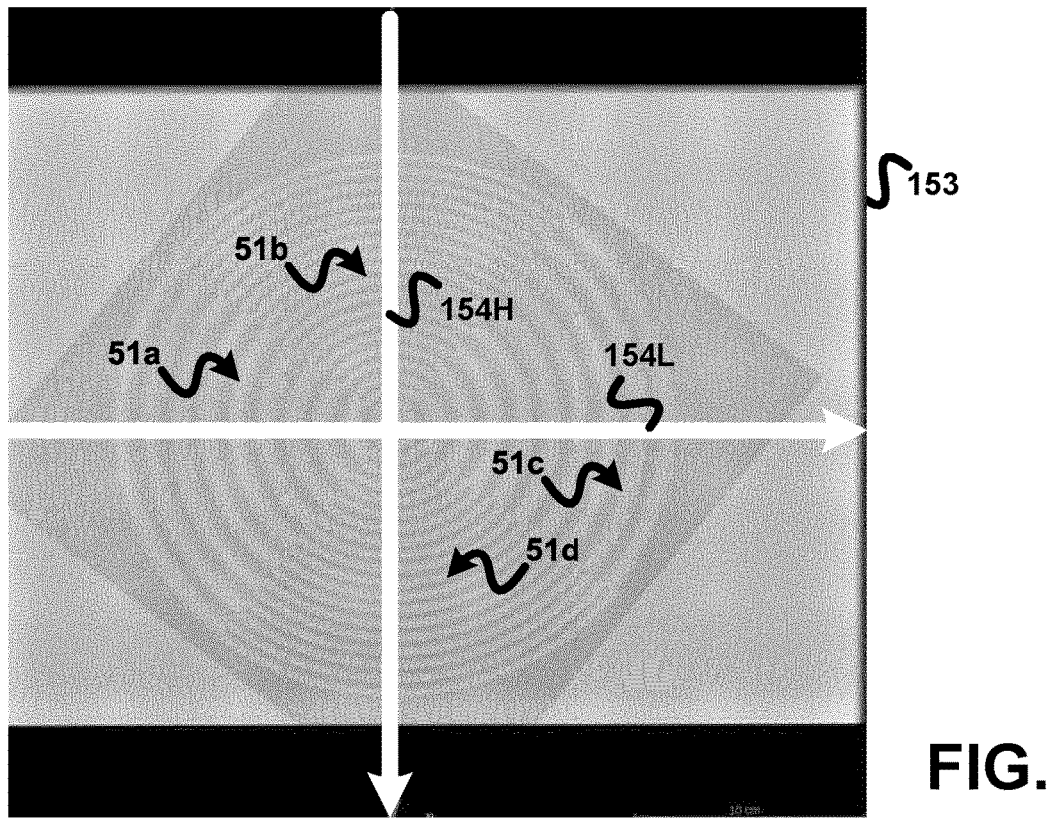
FIGS. 17A and 17B illustrate an exemplary transformation parameter generation of an X-ray ripple marker of FIG. 15A in a second position in accordance with various aspects of the present disclosure.

By further example, FIG. 17A illustrates a scenario where the ripple pattern of X-ray ripple marker 20*b* is parallel with the X-ray detector at a second parallel position 153 with a line 154L traversing through low frequency radial ripple series 51*a* and low frequency radial ripple series 51*c*, and a line 154H traversing through high frequency radial ripple series 51*b* and high frequency radial ripple series 51*d*.

Figure 16B:
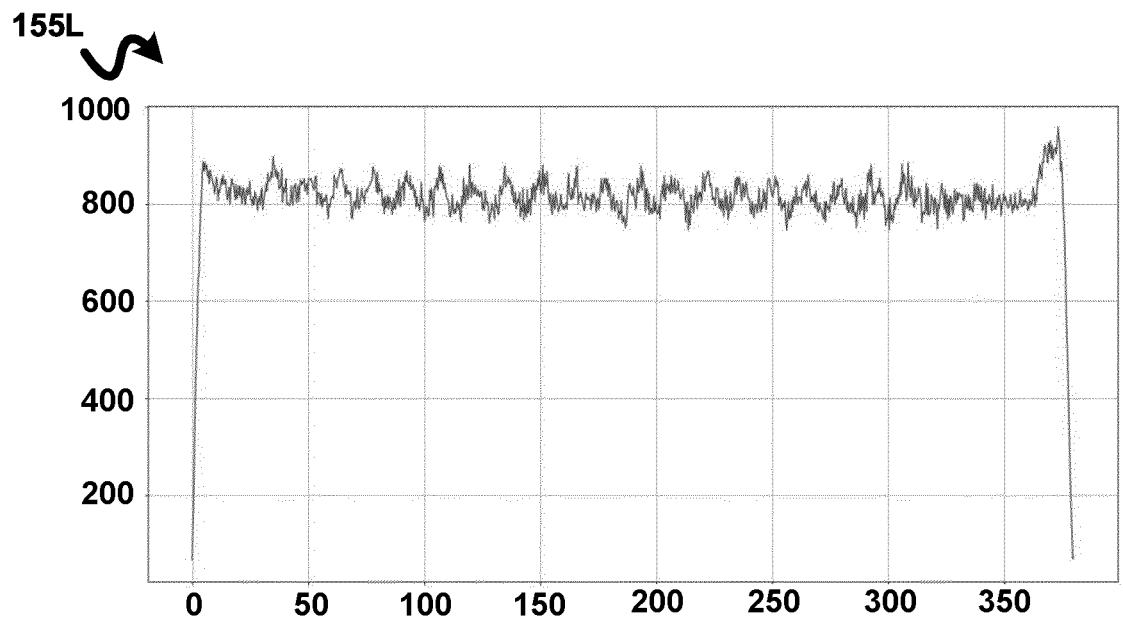
Figure 16B:
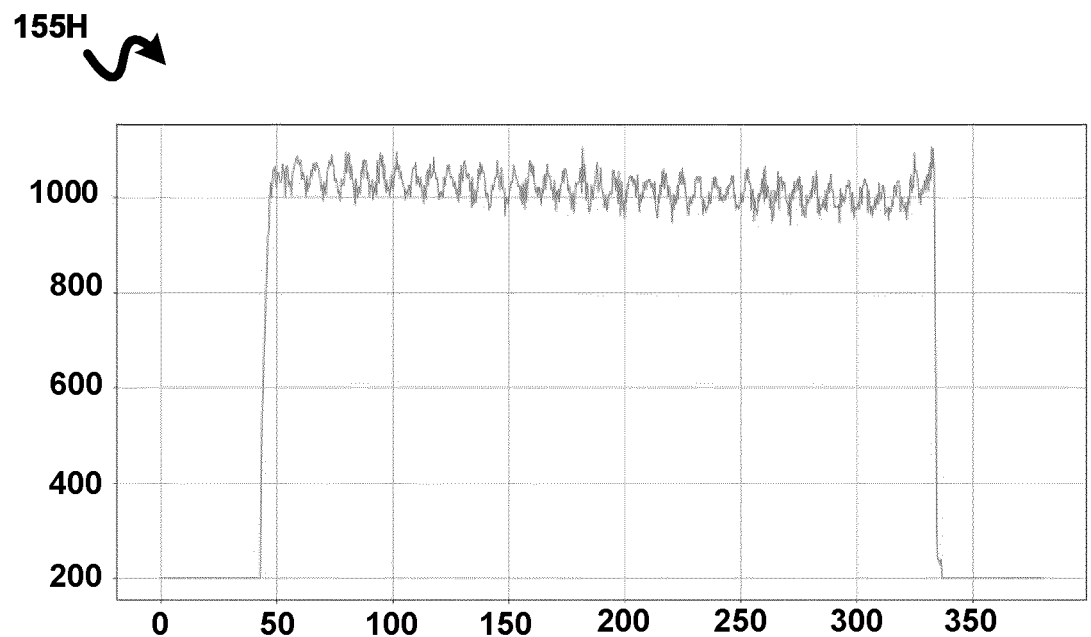

For the first parallel position 151 (FIG. 16A) during stage S142, FIG. 16B shows an intensity plot 155L for low frequency radial ripple series 51*a* and low frequency radial ripple series 51*c* at the first position 151, and intensity plot 155H for high frequency radial ripple series 51*b* and high frequency radial ripple series 51*d*.

Figure 17B:
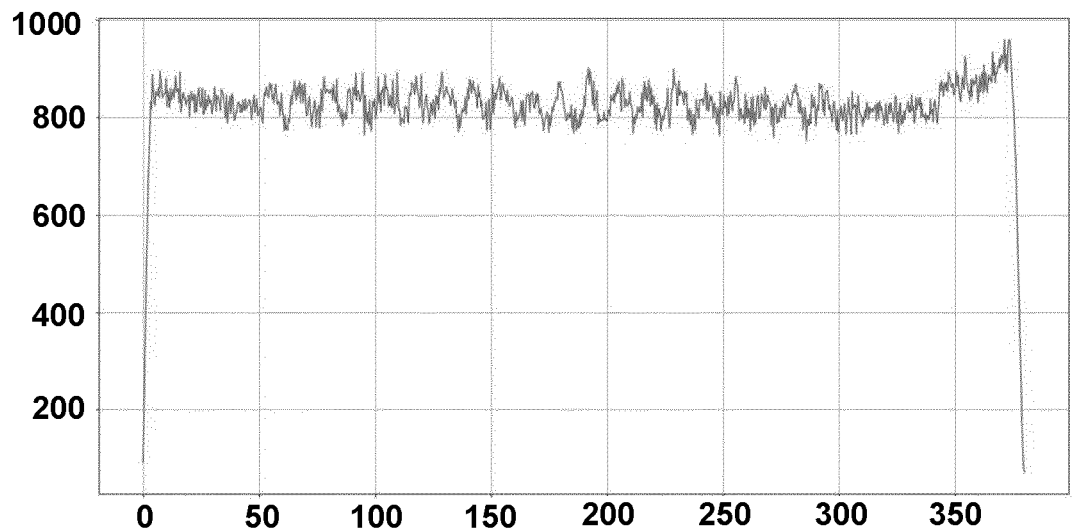
Figure 17B:
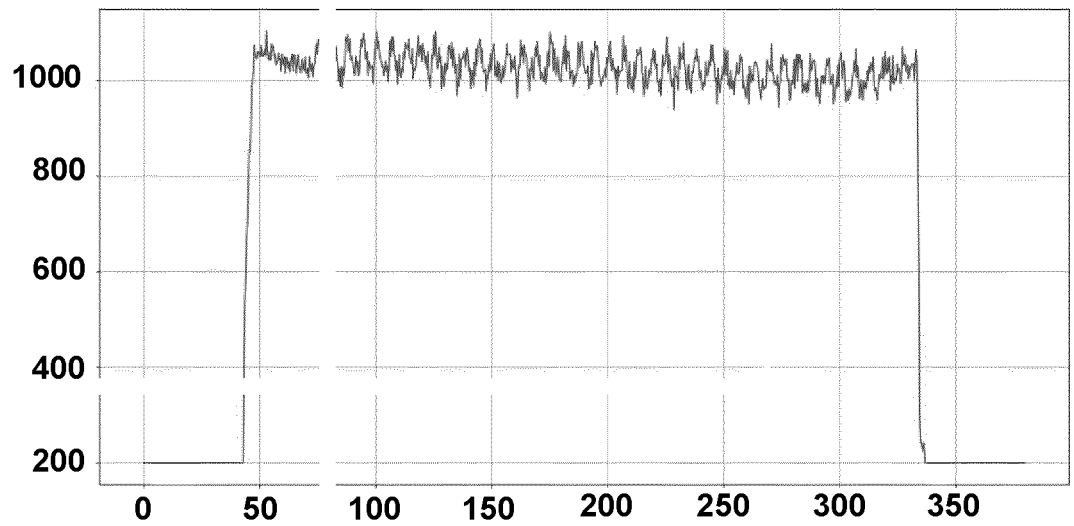

For the second parallel position 152 (FIG. 17A) during stage S142, FIG. 17B shows an intensity plot 156L for low frequency radial ripple series 51*a* and low frequency radial ripple series 51*c* at the first position 151, and intensity plot 156H for high frequency radial ripple series 51*b* and high frequency radial ripple series 51*d*.

Figure 15B:
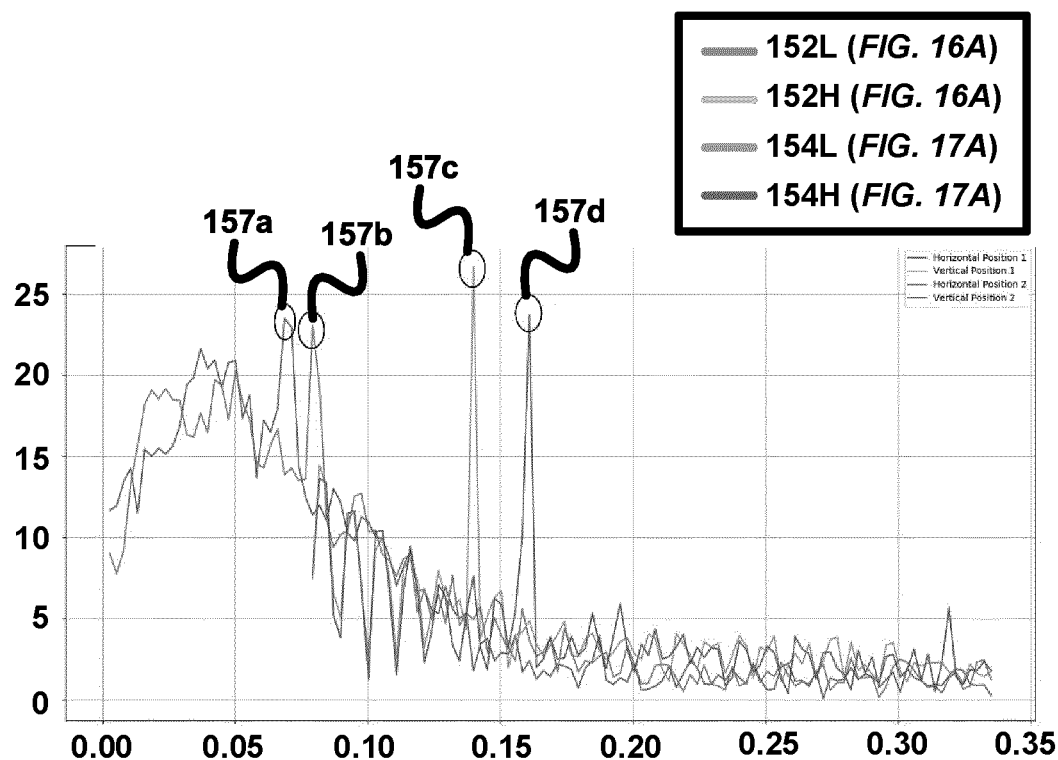

FIG. 15B shows a FFT analysis 157*a* of intensity plot 155L, a FFT analysis 157*b* of intensity plot 155H, a FFT analysis 157*c* of intensity plot 156L and a FFT analysis 157*c* of intensity plot 156H.

For the first position 151 of FIG. 16A, a peak of FFT analysis 157*a* is the lowest image frequency $f_L^I$ of equation [11c] and a peak of FFT analysis 157*b* is the highest image frequency $f_H^I$ of equation [11c].

For the second position 153 of FIG. 17A, a peak of FFT analysis 157*c* is the lowest image frequency $f_L^I$ of equation [11c] and a peak of FFT analysis 157*d* is the highest image frequency $f_H^I$ of equation [11c].

Referring back to FIG. 14, a stage S140 of flowchart S146 encompasses controller 70 registering X-ray ripple marker 20*b* and the X-ray C-arm.

In one embodiment of stage S140, xcd and ycd represent the center of the X-ray ripple marker 20*b* in detector coordinate system whereby the compute the translation of X-ray ripple marker 20*b* is computed in accordance with the following equations [12a]-[12c]:

$$tz = SD - SM \quad [12]$$

$$tx = xcd * SD/SM \quad [12]$$

$$ty = ycd * SD/SM \quad [12]$$

By additional example illustrates a scenario where the ripple pattern of X-ray ripple marker 20b is titled with respect to the X-ray detector at a position 158 with a line 158L traversing through low frequency radial ripple series 51a and low frequency radial ripple series 51c, and a line 158H traversing through high frequency radial ripple series 51b and high frequency radial ripple series 51d.

Figure 18A:
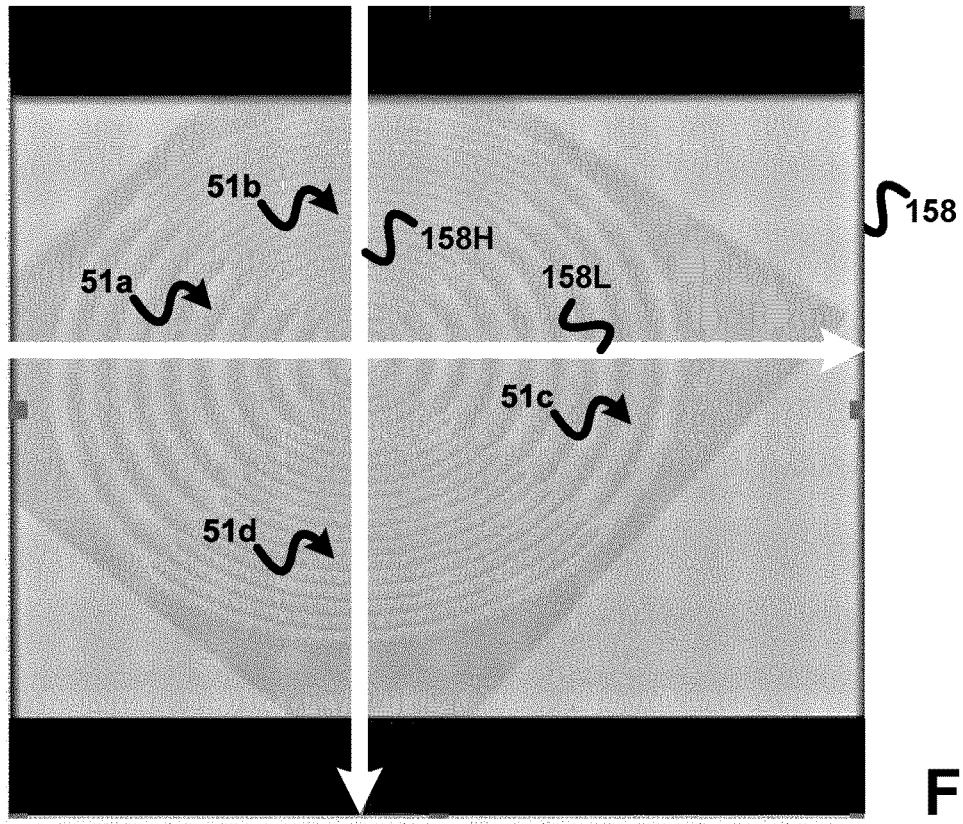
FIGS. 18A and 18B illustrate an exemplary C-arm registration of an X-ray ripple marker of FIG. 15A in a third position in accordance with various aspects of the present disclosure.
Figure 18B:
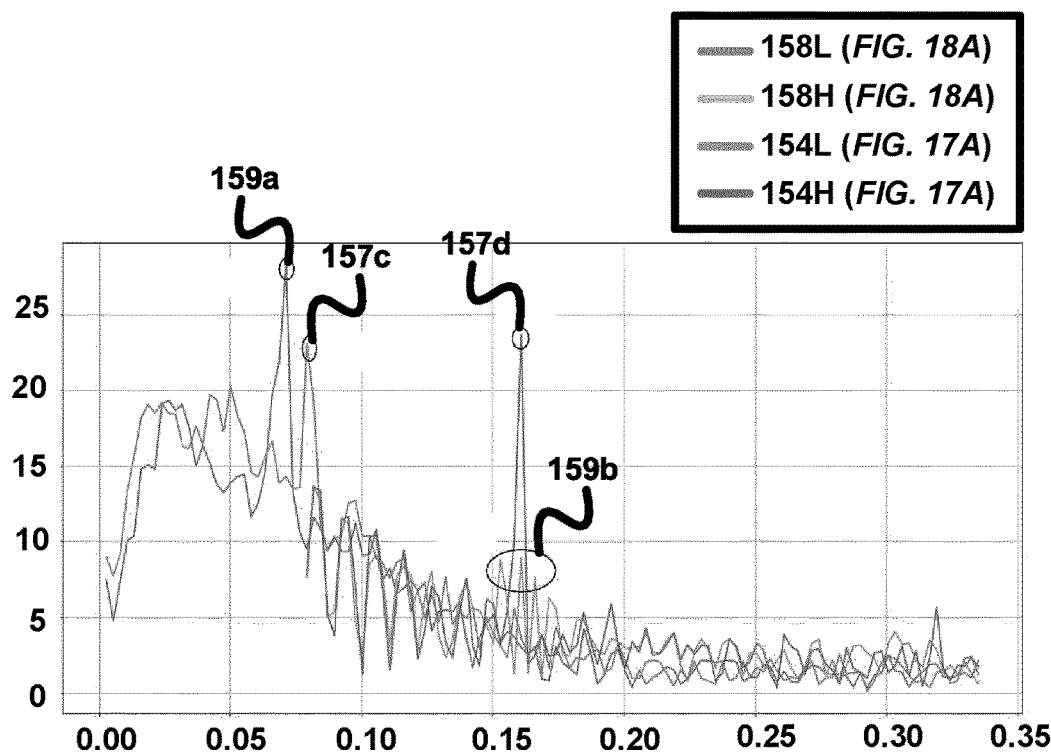

FIG. 18B shows a FFT analysis 159a of an intensity plot for line 158L and a FFT analysis 159b of an intensity plot for line 158H. The rotation axis of FFT analysis 159a is sharp as the rotation of the ripple pattern due to the tilt will not change the frequency of low frequency radial ripple series 51a and low frequency radial ripple series 51c, while the rotation axis of FFT analysis 159b is spread out as the rotation of the ripple pattern due to the tilt will change the frequency of high frequency radial ripple series 51b and high frequency radial ripple series 51d.

Figure 19:
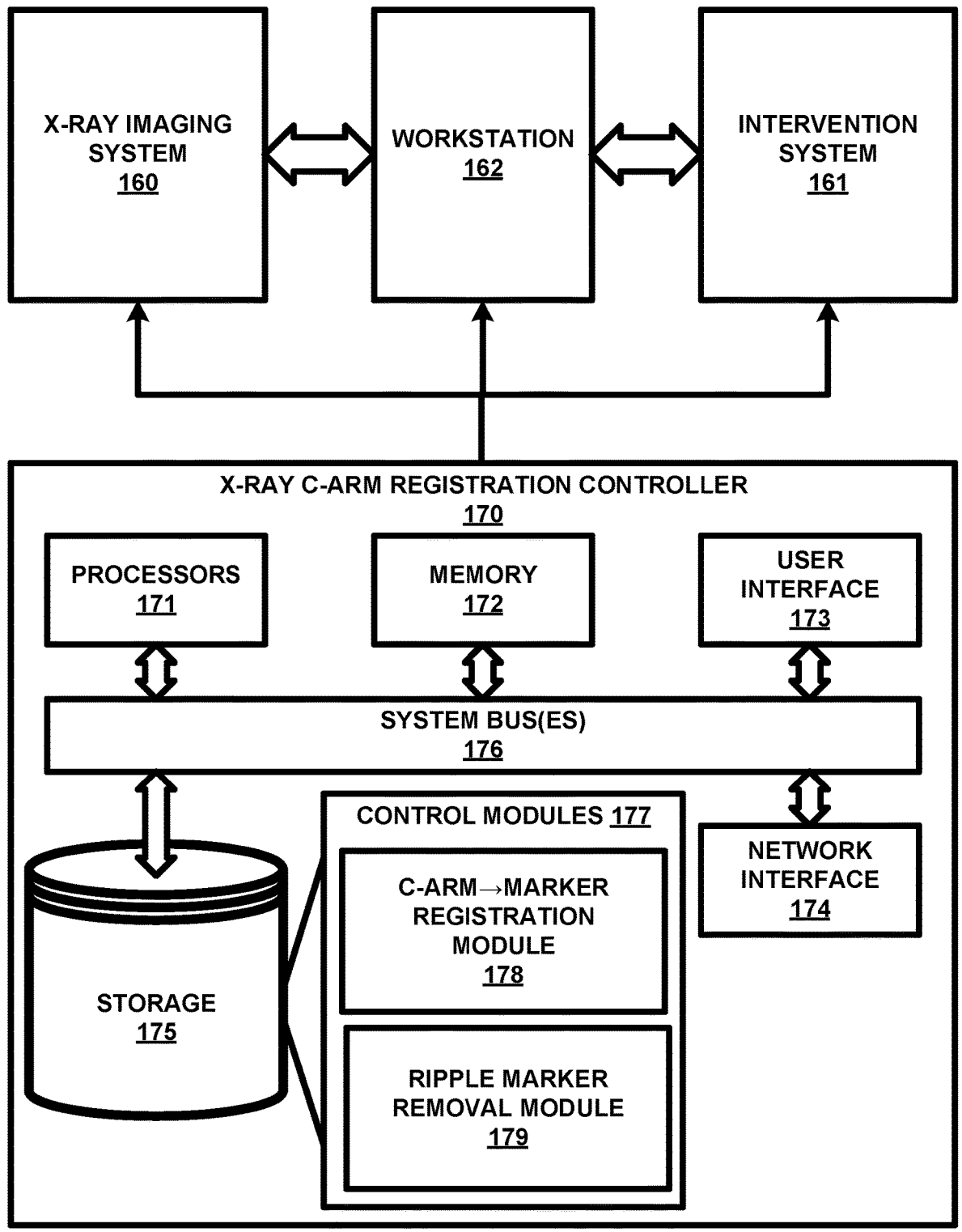
FIG. 19 illustrates an exemplary embodiment of a C-arm registration controller in accordance with various aspects of the present disclosure.

To facilitate a further understanding of the various inventions of the present disclosure, the following description of FIG. 19 teaches an exemplary embodiment of a C-arm registration controller of the present disclosure. From this description, those having ordinary skill in the art will appreciate how to apply various aspects of the present disclosure for making and using additional embodiments of C-arm registration controller of the present disclosure.

Referring to FIG. 19, a C-arm registration controller 170 includes one or more processor(s) 171, memory 172, a user interface 173, a network interface 174, and a storage 175 interconnected via one or more system buses 176.

Each processor 171 may be any hardware device, as known in the art of the present disclosure or hereinafter conceived, capable of executing instructions stored in memory 172 or storage or otherwise processing data. In a non-limiting example, the processor(s) 171 may include a microprocessor, field programmable gate array (FPGA), application-specific integrated circuit (ASIC), or other similar devices.

The memory 172 may include various memories, as known in the art of the present disclosure or hereinafter conceived, including, but not limited to, L1, L2, or L3 cache or system memory. In a non-limiting example, the memory 172 may include static random access memory (SRAM), dynamic RAM (DRAM), flash memory, read only memory (ROM), or other similar memory devices.

The user interface 173 may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface 174.

The network interface 174 may include one or more devices, as known in the art of the present disclosure or hereinafter conceived, for enabling communication with other hardware devices. In a non-limiting example, the network interface 174 may include a network interface card (NIC) configured to communicate according to the Ethernet protocol. Additionally, the network interface 174 may implement a TCP/IP stack for communication according to the TCP/IP protocols. Various alternative or additional hardware or configurations for the network interface 174 will be apparent.

The storage 175 may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage 175 may store instructions for execution by the processor(s) 171 or data upon with the processor(s) 171 may operate. For example, the storage 175 may store a base operating system for controlling various basic operations of the hardware. The storage 175 also stores application modules in the form of executable software/firmware for implementing the various functions of the controller 170a as previously described in the present disclosure including, but not limited to, a C-arm to marker registration module 178 and a ripple marker removal module 179 as previously described in the present disclosure.

In practice, controller 170 may be installed within an X-ray imaging system 160, an intervention system 161 (e.g., an intervention robot system), or a stand-alone workstation 162 in communication with X-ray imaging system 160 and/or intervention system 161 (e.g., a client workstation or a mobile device like a tablet). Alternatively, components of controller 170 may be distributed among X-ray imaging system 160, intervention system 161 and/or stand-alone workstation 162.

Referring to FIGS. 1-19, those having ordinary skill in the art of the present disclosure will appreciate numerous benefits of the inventions of the present disclosure including, but not limited to, an X-ray ripple marker facilitating an accurate and reliable C-arm Registration, particularly for mobile C-arms.

Additionally,

Further, as one having ordinary skill in the art will appreciate in view of the teachings provided herein, structures, elements, components, etc. described in the present disclosure/specification and/or depicted in the Figures may be implemented in various combinations of hardware and software, and provide functions which may be combined in a single element or multiple elements. For example, the functions of the various structures, elements, components, etc. shown/illustrated/depicted in the FIGS. can be provided through the use of dedicated hardware as well as hardware capable of executing software in association with appropriate software for added functionality. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention.

Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Having described preferred and exemplary embodiments of the various and numerous inventions of the present disclosure (which embodiments are intended to be illustrative and not limiting), it is noted that modifications and variations can be made by persons skilled in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device/system or such as may be used/implemented in/with a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A C-arm registration system, comprising:
   an X-ray ripple marker including a ripple pattern radially extending from a fixed point of the X-ray ripple marker; and
   a C-arm registration controller configured to:
      identify the ripple pattern within an X-ray image generated from an X-ray projection by a C-arm and illustrative of at least a portion of the ripple pattern, wherein an identification of the ripple pattern within the X-ray image is characteristic of a pose of the X-ray projection by the C-arm relative to the X-ray rippler marker;
      analyze the ripple pattern within the X-ray image to derive at least one transformation parameter definitive of the pose of the X-ray projection by the C-arm relative to the X-ray rippler marker; and
      register the C-arm to the X-ray ripple marker based on the at least one transformation parameter.

2. The C-arm registration system of claim 1, wherein the ripple pattern includes:
   a plurality of concentric circular ripples.

3. The C-arm registration system of claim 1, wherein the ripple pattern includes:
   a first series of concentric arc ripples.

4. The C-arm registration system of claim 3, wherein the ripple pattern further includes:
   a second series of concentric arc ripples dissimilar to the first series of concentric arc ripples in at least one of frequency, phase and amplitude.

5. The C-arm registration system of claim 1, wherein the X-ray ripple marker further includes:
   a chirp pattern axially aligned with the ripple pattern.

6. The C-arm registration system of claim 1, wherein the X-ray ripple marker further includes:
   a landmark pattern axially aligned with the ripple pattern.

7. The C-arm registration system of claim 1, wherein the C-arm registration controller configured to analyze the ripple pattern within the X-ray image includes the C-arm registration controller further configured to:
   compute at least one wave projection parameter from the identification of the ripple pattern within the X-ray image; and
   derive the at least one transformation parameter from a computation of the at least one wave projection parameter computed from the identification of the rippler pattern within the X-ray image.

8. The C-arm registration system of claim 7, wherein the C-arm registration controller configured to analyze the ripple pattern within the X-ray image further includes the C-arm registration controller further configured to:
   apply a least squares approach to the at least one transformation parameter derived from the computation of the at least one wave projection parameter from the identification of the ripple pattern within the X-ray image.

9. The C-arm registration system of claim 1, wherein the C-arm registration controller configured to analyze the ripple pattern within the X-ray image includes the C-arm registration controller further configured to:
   compute at least one frequency parameter from the identification of the ripple pattern within the X-ray image;
   apply a Fast Fourier Transform to the computation of the at least one frequency parameter from the identification of the ripple pattern within the X-ray image; and
   derive the at least one transformation parameter from an application of the Fast Fourier Transform to the computation of the at least one frequency parameter from the identification of the ripple pattern within the X-ray image.

10. The C-arm registration system of claim 1, wherein the C-arm registration controller is further configured to remove the ripple pattern from the X-ray image.

11. A C-arm registration controller, comprising:
   a non-transitory machine-readable storage medium encoded with instructions for execution by at least one processor of a registration of a C-arm to an X-ray ripple marker including a ripple pattern radially extending from a fixed point of the X-ray ripple marker, the non-transitory machine-readable storage medium comprising instructions to:
      identify the ripple pattern within an X-ray image generated from an X-ray projection by the C-arm and illustrative of at least a portion of the ripple pattern, wherein an identification of the ripple pattern within the X-ray image is characteristic of a pose of the X-ray projection by the C-arm relative to the X-ray rippler marker;
      analyze the ripple pattern within the X-ray image to derive at least one transformation parameter definitive of the pose of the X-ray projection by the C-arm relative to the X-ray rippler marker; and
      register the C-arm to the X-ray ripple marker based on the at least one transformation parameter.

12. The C-arm registration controller of claim 11, wherein the instructions to analyze the ripple pattern within the X-ray image includes instructions to:
   compute at least one wave projection parameter from the identification of the ripple pattern within the X-ray image; and
   derive the at least one transformation parameter from an computation of the at least one wave projection parameter from the identification of the ripple pattern within the X-ray image.

13. The C-arm registration controller of claim 12, wherein the instructions to analyze the ripple pattern within the X-ray image further includes instructions to:
apply a least squares approach to the at least one transformation parameter derived from the computation of the at least one wave projection parameter from the identification of the ripple pattern within the X-ray image.

14. The C-arm registration controller of claim 11, wherein the instructions to analyze the ripple pattern within the X-ray image includes instructions to:
compute at least one frequency parameter from the identification of the ripple pattern within the X-ray image;
apply a Fast Fourier Transform to the computation of the at least one frequency parameter from the identification of the ripple pattern within the X-ray image; and
derive the at least one transformation parameter from an application of the Fast Fourier Transform to the computation of the at least one frequency parameter from the identification of the ripple pattern within the X-ray image.

15. The C-arm registration controller of claim 11, wherein the non-transitory machine-readable storage medium further comprises instructions to:
remove the ripple pattern from the X-ray image.

16. A C-arm registration method executable by a C-arm registration controller for registering a C-arm to an X-ray ripple marker including ripple pattern radially extending from a fixed point of the X-ray ripple marker, the C-arm registration method comprising:
identifying, via the C-arm registration controller, the ripple pattern within an X-ray image generated from an X-ray projection by the C-arm and illustrative of at least a portion of the ripple pattern,
wherein the identification of the ripple pattern within the X-ray image is characteristic of a pose of the X-ray projection by the C-arm relative to the X-ray rippler marker,
analyzing, via the C-arm registration controller, the ripple pattern within the X-ray image to derive at least one transformation parameter definitive of the pose of the X-ray projection by the C-arm relative to the X-ray rippler marker; and
registering, via the C-arm registration controller, the C-arm to the X-ray ripple marker based on the at least one transformation parameter.

17. The C-arm registration method of claim 16, wherein analyzing, via the C-arm registration controller, the ripple pattern within the X-ray image includes:
computing, via the C-arm registration controller, the at least one wave projection parameter from the identification of the ripple pattern within the X-ray image; and
deriving to the at least one transformation parameter from the at least one wave projection parameter computed from the identification of the ripple pattern within the X-ray image.

18. The C-arm registration method of claim 17, analyzing, via the C-arm registration controller, the ripple pattern within the X-ray image further includes:
applying, via the C-arm registration controller, a least squares approach to the at least one transformation parameter derived from the at least one wave projection parameter computed from the identification of the ripple pattern within the X-ray image.

19. The C-arm registration method of claim 16, wherein analyzing, via the C-arm registration controller, the ripple pattern within the X-ray image includes:
computing, via the C-arm registration controller, at least one frequency parameter from the identification of the ripple pattern within the X-ray image;
applying, via the C-arm registration controller, a Fast Fourier Transform to the computation of the at least one frequency parameter from the identification of the ripple pattern within the X-ray image; and
deriving, via the C-arm registration controller, the at least one transformation parameter from an application of the Fast Fourier Transform to the computation of the at least one frequency parameter from the identification of the ripple pattern within the X-ray image.

20. The C-arm registration method of claim 16, further comprising:
removing, via the C-arm registration controller, the ripple pattern from the X-ray image.

* * * * *